(12) United States Patent
Butas et al.

(10) Patent No.: US 7,228,241 B1
(45) Date of Patent: Jun. 5, 2007

(54) SYSTEMS, METHODS AND APPARATUS FOR DETERMINING PHYSICAL PROPERTIES OF FLUIDS

(75) Inventors: John P. Butas, Huntsville, AL (US); Paul D. Van Buskirk, Humble, TX (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 11/152,810

(22) Filed: Jun. 13, 2005

(51) Int. Cl.
*G01F 17/00* (2006.01)
*G01N 11/00* (2006.01)
(52) U.S. Cl. .................................................. 702/50
(58) Field of Classification Search ............... 702/23, 702/27, 45, 47, 50; 73/53.01, 861
See application file for complete search history.

(56) References Cited

U.S. PATENT DOCUMENTS

2005/0279164 A1* 12/2005 Ploechinger ............... 73/488

* cited by examiner

*Primary Examiner*—Michael Nghiem
(74) *Attorney, Agent, or Firm*—James J. McGroary; Ellis B. Ramirez

(57) ABSTRACT

In some embodiments, systems and methods and apparatus are provided through which the equation of state is used to control a process through analyses of one or more properties of a fluid through an interactive modeler that models the equation of state for the fluid in the process based on measured signals and for selectively enabling the modeling of control changes to the process. In some embodiments, a device generates an indication of machine health based on variations on the equation of state for a fluid in a machine. In some embodiments, one or more properties for the fluid from at least one unmeasured machine parameter in the interactive modeler are determined for the machine at various operating states. In some embodiments, a difference between an expected one or more properties of the fluid beyond a set point indicates the health of the machine.

66 Claims, 12 Drawing Sheets

SYSTEMS, METHODS AND APPARATUS FOR DETERMINING PHYSICAL PROPERTIES OF FLUIDS

ORIGIN OF THE INVENTION

The invention described herein was made in part by employees of the United States Government and may be manufactured and used by or for the government for government purposes without payment of any royalties thereon or therefore.

FIELD OF THE INVENTION

This invention relates generally to a computerized method for the determination of volumetric and physical properties of any fluid, and more particularly to an apparatus that determines the physical properties of fluids by the use of signals that are processed by using an extended Lee-Kesler equation of state.

BACKGROUND OF THE INVENTION

Fluid analysis offers important information to the fluid and process engineer in chemical manufacturing facilities. The volumetric and thermodynamic properties of fluids adds to the understanding of complex chemical, physical, and fluid flow processes occurring in a chemical reaction or in the flow of fluids. Fluid analysis has been used to model fluids in reservoirs, in compositional model describing reservoir hydrocarbon content as a multiple-component mixture, in steady state and transient flow in a complex of fluid network, and in managing machine health analyses. Machine health is the analysis of a machine operational status and condition measurement and analysis of operational parameters, including determination of fluid levels and fluid and gas temperatures and pressures for a machine. Through fluid analyses the management of machine health drastically reduces catastrophic downtime, extends drain intervals, and preserves resources.

It is well known that chemical and physical analysis of a machine fluid can provide information about the condition of the fluid as well as the wear status of the machine in which the fluid is used. Machine fluid analysis is widely used for determination of lubricant condition, lubricant contamination and wear status in engines, drive components and hydraulic systems in fleet or industrial service. For example, lubrication oil analysis is widely used for engines and is conducted by the military on most motorized equipment including aircraft and naval engines and lubricated drive components. In industry, commercial fluid analysis providers offer fluid analysis service for engine and drive train lubricants as well as hydraulic fluids. Traditionally, an oil sample is taken from the lubricant or fluid reservoir on the engine being analyzed. The fluid is then subjected to viscosity, chemical degradation, water, and elemental analysis in remote site such as a laboratory. The elemental analysis provides an indication of component wear in a machine according to the type and amount of metals in the sample. The traditional model is, however, difficult to apply in situations where the machine is difficult to obtain access to, such as outer space, and where the information is needed for a quick response.

For the reasons stated above, and for other reasons stated below which will become apparent to those skilled in the art upon reading and understanding the present specification, there is a need in the art for a system and method of fluid analyses that can be performed in real time, is automatic, and does not intrude with operations of the environment. There is also a need for an improved method of determining the equation of states of fluids.

SUMMARY OF THE INVENTION

The above-mentioned shortcomings, disadvantages and problems are addressed herein, which will be understood by reading and studying the following specification.

A computerized method for determining one or more properties of a multi-component fluid by receiving information indicative of the physical properties of a simple fluid, a first reference fluid, and a second reference fluid. Determining the molar volume, departure functions, thermodynamic deviation, and thermodynamic properties of a simple fluid, first reference fluid, and second reference fluid from the received information and operating parameters of a multi-component fluid. The computerized method solves the need in the art for real-time fluid analysis without operational interruptions.

A computerized method for determining one or more properties of a multi-component fluid by selecting an indicator that characterizes the fluid as one of polar fluid, non-polar fluid and receiving information indicative of the physical properties of a simple fluid, a first reference fluid, and a second reference fluid. The indication and physical properties are then used determine molar volume, departure functions, thermodynamic deviation, and thermodynamic property for the multicomponent fluid.

A method of executing real-time control of a process through analyses of one or more properties of a fluid through an interactive modeler that models the equation of state for the fluid in the process based on measured signals and for selectively enabling the modeling of control changes to the process. Further, receiving input signals which represent measured parameter values for a fluid from a plurality of sensors and periodically transmitting said measured parameter values to an interactive modeler having a process model that models the equation of state for the fluid in the process. The interactive modeler estimating one or more properties for the fluid from at least one unmeasured process parameter in said interactive modeler from said process model that models the equation of state for the fluid. Additionally, the interactive modeler can determine the difference between the estimated one or more properties of the fluid and the expected one or more properties of the fluid. After determining a set of current and future manipulated parameter values which will minimize the predicted difference between the estimated one or more properties and the expected one or more properties of the fluid; causing a process control device electrically coupled to said process to implement said manipulated parameter values.

An apparatus for monitoring the health of a machine through analyses of one or more properties of a fluid, the machine through a modeler that models the equation of state for the fluid in the machine based on measured signals. Devices for receiving input signals which represent measured parameter, transmitting said measured parameter values to a modeler having a process model that models the equation of state for the fluid in the machine, for estimating one or more properties for the fluid from at least one unmeasured machine parameter in said modeler from said process model, predicting the difference between the estimated one or more properties of the fluid and the expected one or more properties of the fluid, and determining if the difference between the estimated one or more properties of the fluid and the expected one or more properties of the fluid is beyond a predetermined set point. A device for generating an indication of machine health if the difference is beyond a predetermined point.

Systems, clients, servers, methods, and computer-readable media of varying scope are described herein. In addition to the aspects and advantages described in this summary, further aspects and advantages will become apparent by reference to the drawings and by reading the detailed description that follows.

DETAILED DESCRIPTION OF THE INVENTION

Figure 1:
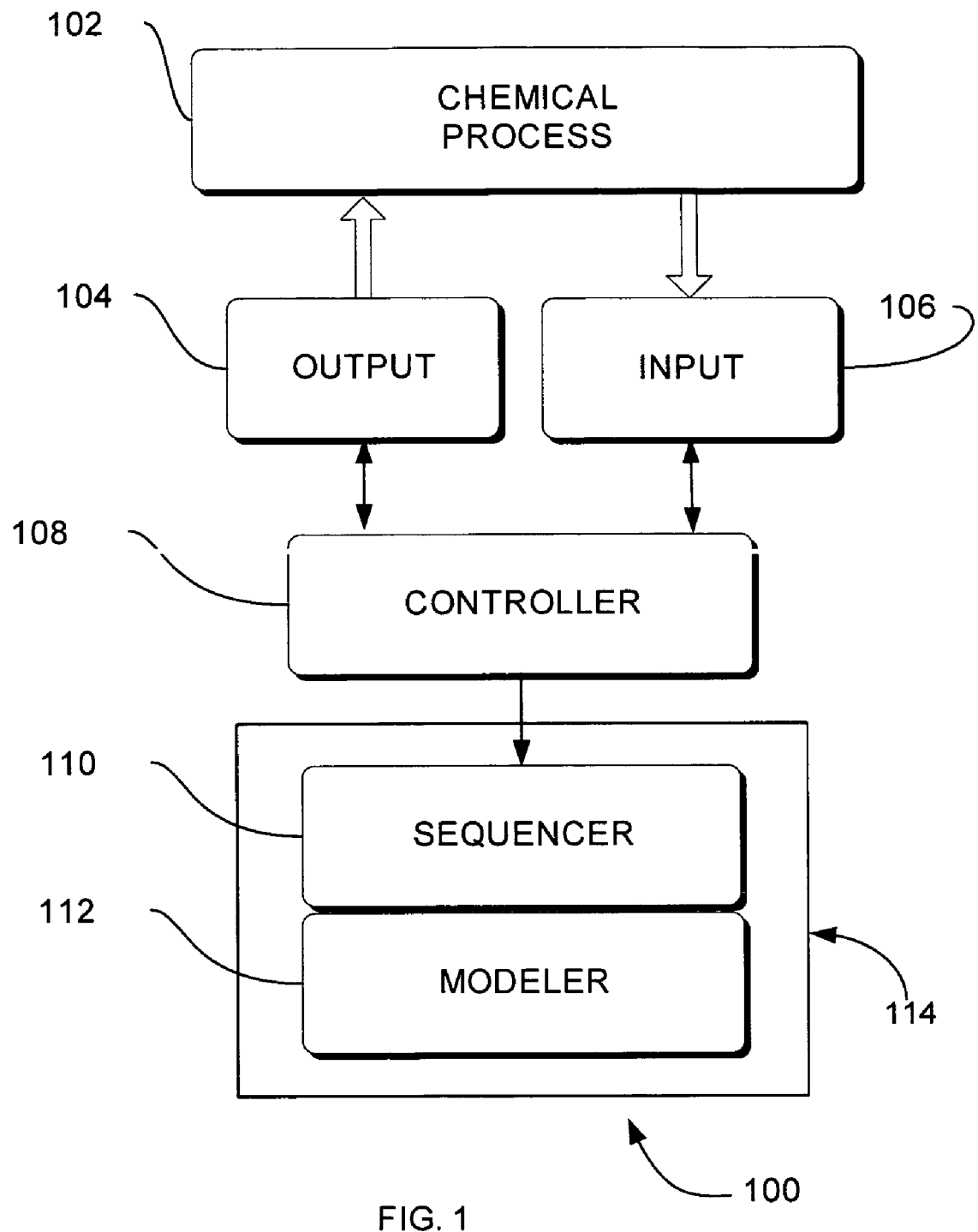
FIG. 1 is a diagram illustrating a system-level overview of an embodiment for determination of physical properties of fluids in a chemical process.

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The compressibility factor of fluids can be described by the following mathematical relationship:

$$Z = Z^{(0)} + \omega Z^{(1)}$$

where $Z^{(0)}$'s the compressibility factor of a simple fluid, $\omega$ is the acentric factor which is related to the shape of the molecule, and $Z^{(1)}$ represents the deviation which is a measure of departure from an ideal gas. This relationship is known as the Lee-Kesler correlation factor for fluids. The relationship, however, is limited to fluids that are substantially non-polar.

By utilization of a modified Taylor Series expansion the Lee-Kesler equation of state can be expanded to include additional terms.

$$X = X^{(0)} + X^{(1)} + X^{(4)} + \frac{\Theta}{\Theta^{(0)}} \cdot (X^{(1)} - X^{(2)} - X^{(3)} + X^{(4)})$$

Where $X^{(O)}$ is the compressibility of a simple fluid, $\Theta$ is a Q factor, and $X^{(i)}$ represent deviation functions. The reference Q factor, $\Theta^{(O)}$, is about 1.16395. The Q factor is within the range of 0.3 to 1.9. However, other ranges and reference Q factors could be selected without departing from the concept.

The deviation function $X^{(i)}$ can be described with following mathematical relationship:

$$X^{(1)} = (\omega - \omega^{(SF)})/(\omega^{(R1)} - \omega^{(SF)}) * (X^{(R1)} - X^{(SF)})$$

$$X^{(2)} = (\sigma - \sigma^{(SF)})/(\sigma^{(R1)} - \sigma^{(SF)}) * (X^{(R1)} - X^{(SF)})$$

$$X^{(3)} = (\omega - \omega^{(SF)})/(\omega^{(R2)} - \omega^{(SF)}) * (X^{(R2)} - X^{(SF)})$$

$$X^{(4)} = (\sigma - \sigma^{(SF)})/(\sigma^{(R2)} - \sigma^{(SF)}) * (X^{(R2)} - X^{(SF)})$$

Where SF is a simple fluid, R1 is a first reference fluid, and R2 is a second reference fluid. $X^{[R2]}$ refers to the compressibility of the second reference fluid, etcetera.

Examples correlating factors for Argon as the simple fluid, Octane as the first reference fluid, and Water as the second reference fluid are:

| Component | Superscript | Acentric Factor ($\omega$) | Radius-of-Gyration ($\sigma$) | Q Factor ($\Theta$) |
|---|---|---|---|---|
| Argon | (0) | −0.004605018 | 1.076 | 1 |
| Octane | (R) | 0.397732487 | 4.546 | 1 |
| Water | (W) | 0.3214248 | 0.615 | 1 |

The radius of gyration ($\sigma$) of fluids is provided in the Yaws database. The acentric factor ($\omega$) is calculated from Yaws critical and normal boiling-point properties by use of the following Lee-Kesler expression:

$$\omega = (-\ln(P_c) - 5.92714 + 6.09648/T_{nbr} + 1.28862 * \ln(T_{nbr}) - 0.169347 * T_{nbr}^6)/(15.2518 - 15.6875/T_{nbr} - 13.4721 * \ln(T_{nbr}) + 0.43577 T_{nbr}^6)$$

Where $P_c$ is the critical pressure and $T_{nbr}$ is the normal boiling point of the fluid for which the compressibility is being determined.

The compressibility factor for a variety of fluids is adequately represented and known to those in the art. The compressibility factor for the simple fluid, the first reference fluid, and the second reference fluid can be calculated from the following modification of the Benedict-Webb-Ruben (BWR) equation-of-state:

$$Z = (P_r V_r / T_r) = 1 + B/V_r + C/V_r^2 + D/V_r^5 + c4/(T_r^3 V_r^2)(\beta + \gamma/V_r^2)\exp(-\gamma/V_r^2)$$

Where $V_r(V/V_c)$ is the reduced volume, $Tr(T/T_c)$ is the reduced temperature, and $P_r(P/P_c)$ is the reduced pressure.

Where the constants B, C, and D are determined from the following relationship:

$$B = b1 - b2/T_r - b3/T_r^2 - b4/T_r^3$$

$$C = c1 - c2/T_r + c3/T_r^3$$

$$D = d1 + d2/T_r$$

When Argon is used as the simple fluid, Octane as the first reference fluid, and Water is used as the second reference fluid, the following table are typical values assuming an arbitrary reduced volume, reduced temperature, and reduced pressure:

| Constant | Argon | Octane | Water |
|---|---|---|---|
| $b_1$ | 0.1181193 | 0.2026579 | 0.1263781 |
| $b_2$ | 0.265728 | 0.331511 | 0.1786672 |
| $b_3$ | 0.15479 | 0.027655 | 0.1308736 |
| $b_4$ | 0.030323 | 0.203488 | 0.1944523 |
| $c_1$ | 0.0236744 | 0.0313385 | −0.00355054 |
| $c_2$ | 0.0186984 | 0.0503618 | −0.000736033 |
| $c_3$ | 0 | 0.016901 | 0.017420037 |
| $c_4$ | 0.042724 | 0.041577 | 0.006247606 |
| $d_1 \times 10^4$ | 0.155488 | 0.48736 | 0.131647 |
| $d_2 \times 10^4$ | 0.623689 | 0.0740336 | −0.0391698 |
| $\beta$ | 0.65392 | 1.226 | 6.6484506 |
| $\gamma$ | 0.060167 | 0.03754 | 0.01861792 |

The thermodynamic departure function can be determined from the following relationships:

Fugacity Coefficient $\ln(f/P) = Z - 1 - \ln(Z) + B/V_r + C/(2V_r^2) + D/(5V_r^5) + E$ Where $E = c4/(2T_r^3 \gamma)\{\beta + 1 - (\beta + 1 - (\beta + 1 + \gamma/V_r^2)\exp(-\gamma/V_r^2)\}$ Enthalpy Departure $(H - H^\circ)/RT_c = T_r\{Z - 1 - (b2 + 2b3/T_r + 3b4/T_r^2)/(T_r V_r) - (c2 - 3c3/T_r^2)/(2T_r V_r^2) + d2/(5T_r V_r^5) + 3E\}$ Entropy Departure $(S - S^\circ)/R + \ln(P/P^\circ) = \ln(Z) - (b1 + b3/T_r^2 + 2b4/T_r^3)/V_r - (c1 - 2c3/T_r^3)/(2V_r^2) - d1/(5V_r^5) + 2E$ Isochoric Heat Capacity Departure $(C_v - C_v^\circ)/R = 2(b3 + 3b4/T_r)/(T_r^2 V_r) - 3c3/(T_r^3 V_r^2) - 6E$ Isobaric Heat Capacity Departure $(C_p - C_p^\circ)/R = (C_v - C_v^\circ)/R - 1 - T_r((\partial P_r/\partial T_r)_{V_r})^2/(\partial P_r/\partial V_r)_{T_r}$ Where $(\partial P_r/\partial T_r)_{V_r} = (1/V_r)\{1 + (b1 + b3/T_r^2 + 2b4/T_r^3)/V_r + (c1 - 2c3/T_r^3)/V_r^2 + d1/V_r^5 - 2c4/(T_r^3 V_r^2)[(\beta + \gamma/V_r^2)\exp(-\gamma/V_r^2)]\}$ $(\partial P_r/\partial V_r)_{T_r} = -(T_r/V_r^2)\{1 + 2B/V_r + 3C/V_r^2 + 6D/V_r^5 + c4/(T_r^3 V_r^2)[3\beta + \{5 - 2(\beta + \gamma/V_r^2)\}\gamma/V_r^2]\exp(-\gamma/V_r^2)\}$ where $P^\circ = 1$ atm, $H^\circ =$ the ideal-gas enthalpy, $S^\circ =$ the ideal-gas entropy, $C_v^\circ =$ ideal-gas constant volume specific heat, and $C_p^\circ =$ ideal-gas constant pressure specific heat, all at the reduced temperature, $T_r$.

The physical properties of the fluid can be calculated from the above relationships.

Thermodynamic Property $$X = X^{(0)} + X^{(1)} + X^{(4)} + \frac{\Theta}{\Theta^{(0)}} \cdot (X^{(1)} - X^{(2)} - X^{(3)} + X^{(4)})$$

Transport Properties

The reference temperature is calculated from the following relationship for the simple fluid, the first reference fluid, and the second reference fluid. The transport properties include viscosity, thermal conductivity, and surface tension.

$$T^{(SF)} = T_C^{(SF)} * (T/T_C^{(SF)})$$

$$T^{(R1)} = T_C^{(R1)} * (T/T_C^{(R1)})$$

$$T^{(R2)} = T_C^{(R2)} * (T/T_C^{(R2)})$$

A log reduced transport property is based on:

$X^{(SF)} = \text{Log}(f(T^{(SF)}))$, for the simple fluid $X^{(R1)} = \text{Log}(f(T^{(R1)}))$, for the first reference fluid $X^{(R2)} = \text{Log}(f(T^{(R2)}))$, for the second reference fluid.

If the fluid is a quantum fluid then the acentric factor ($\omega$) is substantially set to zero. The reduced temperature and pressure of these fluids are corrected using a modified Gunn relation:

$$T_r' = T_r(1 + T_{c1}(MwT_rT_c))$$

$$P_r' = P_r(1 + T_{c2}/(MwT_rT_c))$$

where $T_{c1} = 39.3496$ and $T_{c2} = 78.4586$. The corrected reduced temperature and pressure are used for determination of the volumetric and thermodynamic properties of the quantum fluids, such as hydrogen and helium. For selected quantum fluids, regressed correction factors are included in the Yaws database.

The above mathematical expression can be programmed in any suitable computer to act as individual modules, as one whole program, or a combination of modules. As such these modules may be used by other modules as functions in accordance with the chosen software with "CALL" and "RETURNS" for specific values or parameters. The mathematical expressions can be implemented in spreadsheet programs such as Microsoft Excel® in the form of macros, modules, or procedures that can retrieve data from a worksheet, database query, or from an external source like the internet.

FIG. 1 is a block diagram that provides a system level overview. Embodiments operate in a multi-processing, multi-threaded operating environment on a computer, such as computer 208 in FIG. 3. FIG. 1 is a block diagram of a chemical process control system 100 with a controller 108, a sequencer 110, an interactive modeler 112, and input/output devices (104, 106).

In FIG. 1, the devices are arranged to control a chemical process 102 by employing the principles enumerated in the equations of state for a simple fluid, a first reference fluid, and a second reference fluid. The chemical process 102 can be a batch reactor, a catalytic process, a chemical distiller, chemical plant, a petroleum producing process, or any other process that is used to convert a fluid to another compound or state. A chemical process 102 should be understood that it is only intended to be exemplary of a wide variety of process control applications using the equations of state. In order to control the chemical process, various sensors are provided to measure physical process parameters, such as temperature, pressure, and flow rate.

The signals from these sensors are transmitted to one or more input circuits 106. The input circuits 106 will perform any necessary filtering, averaging and/or conversion to a digital representation of the phenomena being sensed. Then, these digital input signals will be transmitted to a controller 108, which will make process control decisions, based at least in part upon the magnitude of the digital input signals in conjunction with the equations of state. The controller 108 employs one or more PID algorithms in order to maintain desired set points for specific controlled parameters, such as temperature, pressure and fluid delivery rates. PID (Proportional Integral Derivative Control) is popular control strategy that produces output control action proportional to the sum of the input, plus the integral of the input, plus the rate of change of the input. Each of these PID algorithms will attempt to follow a set-point profile, which may be a function of various "measured" parameter values. Once these control decisions are made, the controller 108 will transmit the appropriate command signals to one or more output circuits 104. The output circuits will perform any needed signal conversion (A/D, D/A), and the output circuits may also contain slave controllers for achieving the set points commanded by the controller 108. Then, these processed output signals will be transmitted to control devices, such as pumps, valves, relays and motors. For example, if the controller 108 determines that the temperature within the chemical process 102 needs to be increased, then an appropriate command signal will be transmitted to the output circuit 104. This command signal may take the form of a set point to be achieved, if the output circuit 104 is equipped with a slave controller. Otherwise, this command signal may be a signal which directly manipulates a physical device, such as an electronically actuated valve.

However, in FIG. 1, the process control system 100 is equipped with an interactive modeler 114 which enables the controller 108 to anticipate and respond to future process events. The interactive modeler 114 generally includes a sequencer 110 and a modeler 112. The sequencer 110 is adapted to receive a set of real-time process data that has been time stamped from controller 108. This process data is referenced to and stored in a real-time database by the sequencer 110. The sequencer 110 then transmits some or all of this real-time data to the modeler 112 at predetermined intervals.

The interactive modeler 114 includes both a process model and a disturbance model. The process model represents the dynamic behavior of the physical process, while the disturbance model represents current as well as potential future deviations from the process model. In this regard, the sequencer 110 uses the modeler 112 to determine an optimal estimation of the current state of the process and the current disturbances acting on the process. The current state of the process is generally represented by one or more derived or unmeasured parameter values, such as the volumetric and thermodynamic property determined from the equations of state. The sequencer 110 may then forward these unmeasured parameter values to the process controller 108 for use in its control program. As will be more fully explained below, the controller 108 will continue to make process control decisions which are independent of those made by the interactive modeler 114. These process control decisions may be used in lieu of those provided by the interactive controller 114 under the appropriate circumstances.

At given process intervals, the predictive modeler 114 will be used to determine a set of optimized manipulated parameter values over a predetermined prediction horizon. These manipulated parameter values may take the form of a setting for a directly controllable parameter, such as the temperature of the chemical process, flow rate produced by pumps or valves, or derived parameters such as transport values and thermodynamic property. In order to generate this set of optimized manipulated parameter values, the sequencer 110 will project a set of desired controlled parameter values over a predetermined control horizon. These controlled parameter values may take the form of a set point for an indirectly controlled parameter, such as the temperature within the chemical process 102. In other words, this set of controlled parameter values will provide a particular set-point profile that the process control system 100 should seek to track and match.

The sequencer 110 will then forward this set of controlled parameter values to the modeler 112. The modeler 112 will in turn solve a series of equations based upon the above physical laws to determine how the physical process will react to various alternative control changes. The modeler 112 decides the next set of control changes and attempts to provide an optimized set of control changes. As a result, the modeler 112 will transmit an optimal set of control changes over the prediction horizon to the sequencer 110. These future control moves are selected to minimize future set-point deviations given certain physical or programmed constraints. The sequencer 110 will transmit the current set of manipulated parameter values to the controller 108 for implementation. Since the sequencer 110 can be another computer or operator interface it is also possible for the sequencer to be able to inspect the recommended parameter values for reasonableness.

Figure 2:
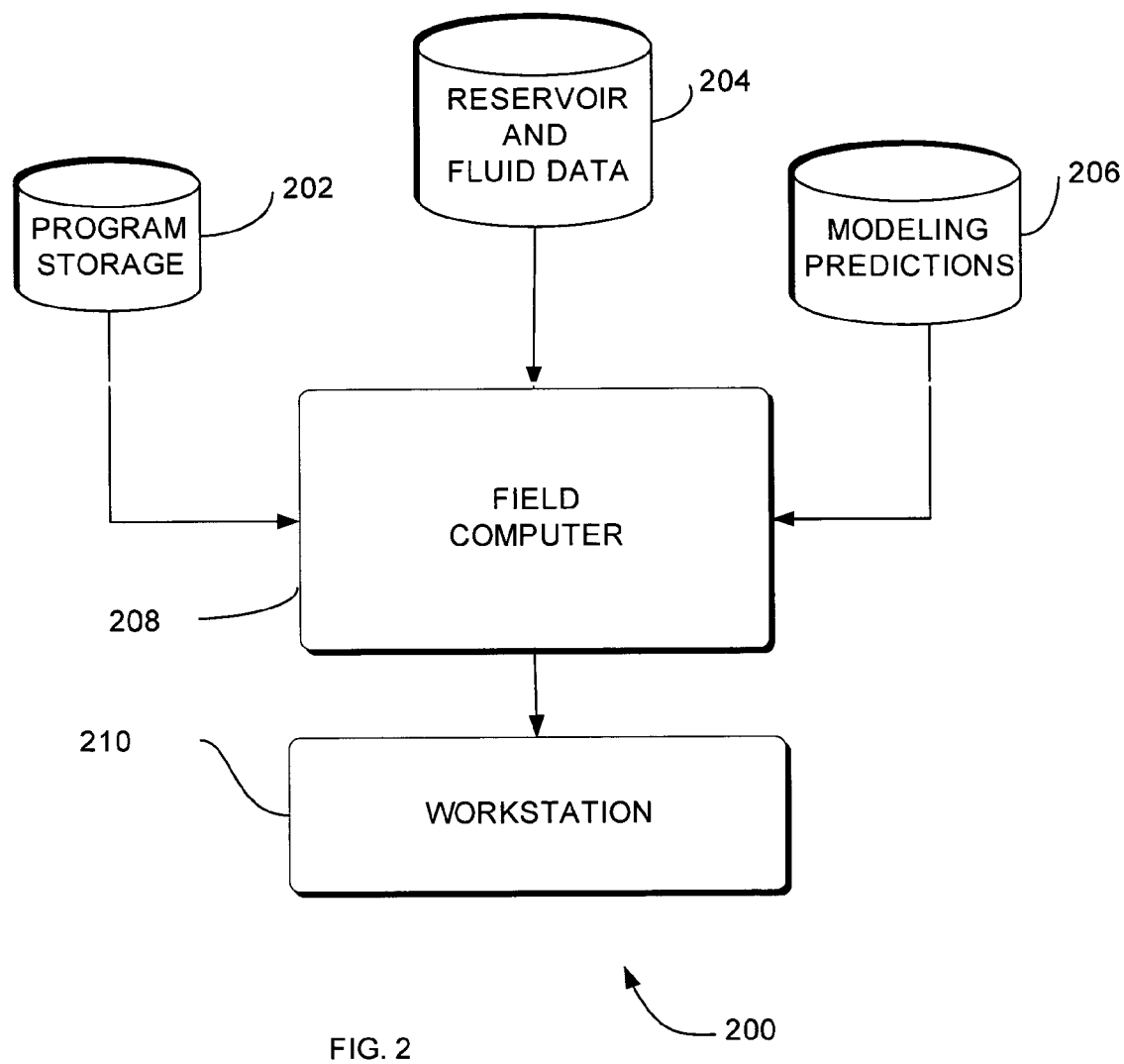
FIG. 2 is a system-level overview of computerized system for petroleum reservoir predictor using equations of state.

FIG. 2 is a block diagram that provides a system level overview. Embodiments are described as operating in a multi-processing, multi-threaded operating environment on a computer, such as computer 208 in FIG. 3. FIG. 2 is a block diagram of a petroleum reservoir predictor that employs a field computer 208, program storage unit 202, reservoir and fluid data collector 204, and modeling predictor 206, that has connection to a remote computer such as a workstation 210. Other than the modeling predictor, items 202, 204, and field computer are conventional and well known to those in the art. The modeling predictor is a computer program that resides in memory (RAM, ROM, and Hard Drive) that can be installed or downloaded from a remote area. The modeling predictor is based on the equations of state that were enumerated above. However, in the art of reservoir modeling it is well known that the region can be constructed by the computer as a collection of volume cells. Each cell has a unique equation of state. Following the assignment of temperature and pressure values to each volume cell in a reservoir construct model, the computer then, for each volume cell, define the volumes and densities of the fluids in place by solving the equations of state for each of the components of the fluids.

Hardware and Operating Environment

Figure 3:
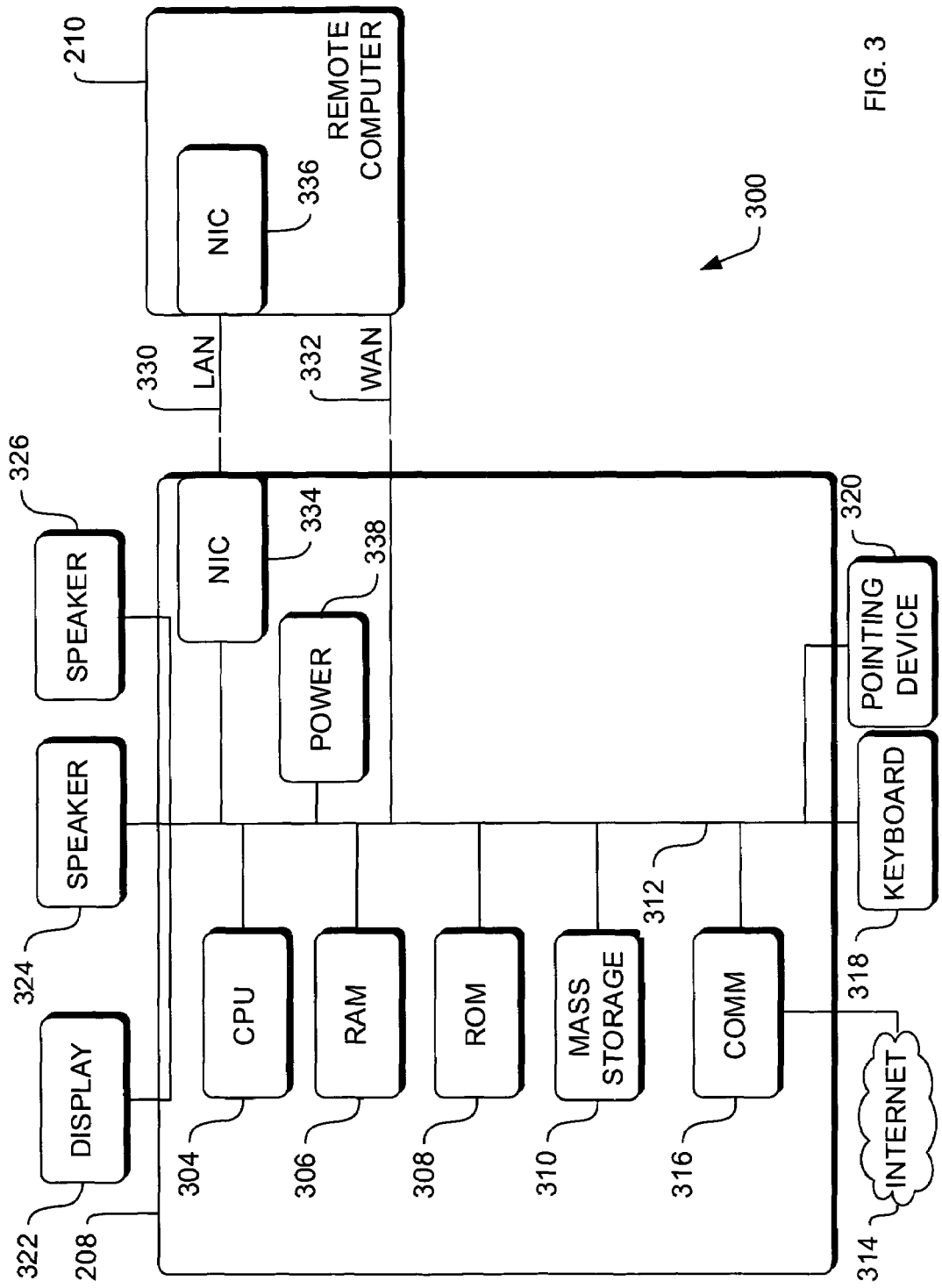
FIG. 3 is a block diagram of the hardware and operating environment in which different embodiments can be practiced.

FIG. 3 is a block diagram of the hardware and operating environment 300 in which different embodiments can be practiced. The description of FIG. 3 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Computer 208 includes a processor 304, commercially available from Intel, Motorola, Cyrix and others. Computer 208 also includes random-access memory (RAM) 306, read-only memory (ROM) 308, and one or more mass storage devices 310, and a system bus 312, that operatively couples various system components to the processing unit 304. The memory 306, 308, and mass storage devices, 310, are types of computer-accessible media. Mass storage devices 310 are more specifically types of nonvolatile computer-accessible media and can include one or more hard disk drives, floppy disk drives, optical disk drives, and tape cartridge drives. The processor 304 executes computer programs stored on the computer-accessible media.

Computer 208 can be communicatively connected to the Internet 314 via a communication device 316. Internet 314 connectivity is well known within the art. In one embodiment, a communication device 316 is a modem that responds to communication drivers to connect to the Internet via what is known in the art as a "dial-up connection." In another embodiment, a communication device 316 is an Ethernet® or similar hardware network card connected to a local-area network (LAN) that itself is connected to the Internet via what is known in the art as a "direct connection" (e.g., T1 line, etc.).

A user enters commands and information into the computer 208 through input devices such as a keyboard 318 or a pointing device 320. The keyboard 318 permits entry of textual information into computer 208, as known within the art, and embodiments are not limited to any particular type of keyboard. Pointing device 320 permits the control of the screen pointer provided by a graphical user interface (GUI) of operating systems such as versions of Microsoft Windows®. Embodiments are not limited to any particular pointing device 320. Such pointing devices include mice, touch pads, trackballs, remote controls and point sticks. Other input devices (not shown) can include a microphone, joystick, game pad, satellite dish, scanner, or the like.

In some embodiments, computer 208 is operatively coupled to a display device 322. Display device 322 is connected to the system bus 312. Display device 322 permits the display of information, including computer, video and other information, for viewing by a user of the computer. Embodiments are not limited to any particular display device 322. Such display devices include cathode ray tube (CRT) displays (monitors), as well as flat panel displays such as liquid crystal displays (LCD's). In addition to a monitor, computers typically include other peripheral input/output devices such as printers (not shown). Speakers 324 and 326 provide audio output of signals. Speakers 324 and 326 are also connected to the system bus 312.

Computer 208 also includes an operating system (not shown) that is stored on the computer-accessible media RAM 306, ROM 308, and mass storage device 310, and is executed by the processor 304. Examples of operating systems include Microsoft Windows®, Apple MacOS®, Linux®, UNIX®. Examples are not limited to any particular operating system, however, and the construction and use of such operating systems are well known within the art.

Embodiments of computer 208 are not limited to any type of computer 208. In varying embodiments, computer 208 comprises a PC-compatible computer, a MacOS®-compatible computer, a Linux®-compatible computer, or a UNIX®-compatible computer. The construction and operation of such computers are well known within the art.

Computer 208 can be operated using at least one operating system to provide a graphical user interface (GUI) including a user-controllable pointer. Computer 208 can have at least one web browser application program executing within at least one operating system, to permit users of computer 208 to access intranet or Internet world-wide-web pages as addressed by Universal Resource Locator (URL) addresses. Examples of browser application programs include Netscape Navigator® and Microsoft Internet Explorer %.

The computer 208 can operate in a networked environment using logical connections to one or more remote computers, such as remote computer 210. These logical connections are achieved by a communication device coupled to, or a part of, the computer 208. Embodiments are not limited to a particular type of communications device. The remote computer 210 can be another computer, a server, a router, a network PC, a client, a peer device or other common network node. The logical connections depicted in FIG. 3 include a local-area network (LAN) 330 and a wide-area network (WAN) 332. Such networking environments are commonplace in offices, enterprise-wide computer networks, intranets and the Internet.

When used in a LAN-networking environment, the computer 208 and remote computer 210 are connected to the local network 330 through network interfaces or adapters 334, which is one type of communications device 316. Remote computer 210 also includes a network device 336. When used in a conventional WAN-networking environment, the computer 208 and remote computer 210 communicate with a WAN 332 through modems (not shown). The modem, which can be internal or external, is connected to the system bus 312. In a networked environment, program modules depicted relative to the computer 208, or portions thereof, can be stored in the remote computer 210.

Computer 208 also includes power supply 338. Each power supply can be a battery.

Methods of an Embodiment

In the previous section, a system level overview of the operation of an embodiment was described. In this section, the particular methods performed by the server and the clients (108, 114, 208, 210) of such an embodiment are described by reference to a series of flowcharts. Describing the methods by reference to a flowchart enables one skilled in the art to develop such programs, firmware, or hardware, including such instructions to carry out the methods on suitable computerized clients, or the processor of the clients executing the instructions from computer-readable media. Similarly, the methods performed by the server computer programs, firmware, or hardware are also composed of computer-executable instructions. Methods 400, 404, 406, 408, 410, 412, 1000, 1100 and 1200 are performed by a client program executing on, or performed by firmware or hardware that is a part of, a computer, such as computer 208 in FIG. 3, and is inclusive of the acts required to be taken by chemical process control system 100, and petroleum reservoir predictor 200.

Figure 4:
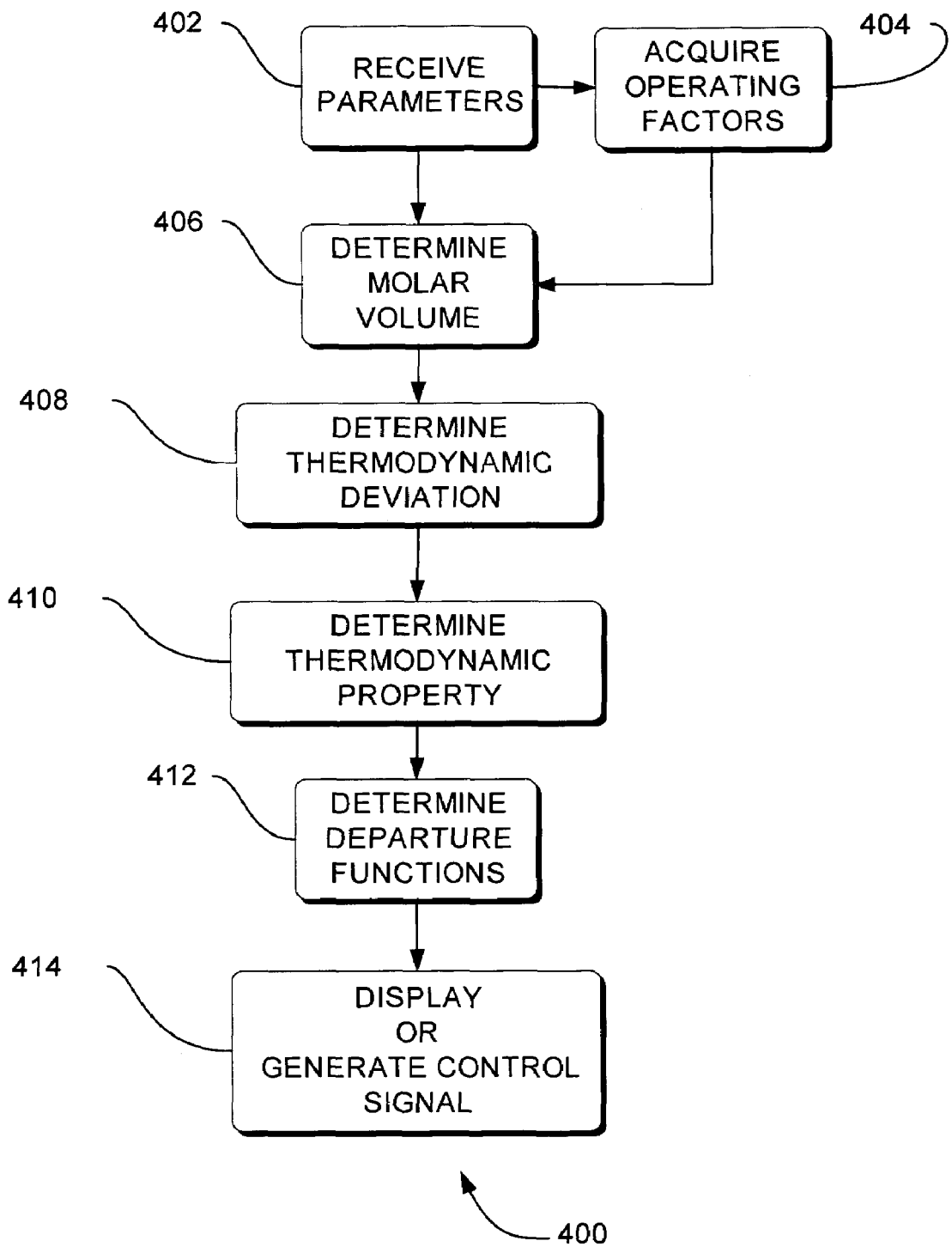
FIG. 4 is a flowchart of an embodiment for determining properties of a fluid by following the equation of state.

FIG. 4 is a flowchart of a method performed by a client according to an embodiment. Method 400 satisfies the need in the art for performing fluid analyses in real-time with minimal interference to the operating environment. Method 400 can be used to control, in conjunction with controllers, actuators, valves, and other devices of chemical process control system 100.

Method 400 begins with action 402 where parameters are received. The received parameters can be a one or combination of temperature, pressure, simple fluid, first reference fluid, second reference fluid, an indication that the fluid is a quantum fluid, Q factor, fluid flow, volume flow, operating environment of the fluid. The received parameters can be inputted through a keyboard 318, pointing device 320, portable digital assistance (PDA), or remote terminal, directly measured from a process or machine, derived from any of the above parameters. Once the parameters have been received control passes to action 404 for further processing.

In action 404, the operating parameters are acquired. In action 404 the received parameters from action 402 such as identification of the fluids (simple, first reference, and second reference), temperature, and pressure are used to acquire values that can facilitate the determination of volumetric and thermodynamic property of the fluid. Once the operating parameters are acquired control passes to action 406 for further processing. Check capitalization throughout—prefer no capitalization unless in accordance with accepted rules.

In action 406 the molar volume is determined. In action 406 the parameters and operating condition are used to determine the molar volume for the simple fluid, the first reference fluid, and the second reference fluid. After the volumes are determined control passes to action 408 for further processing.

In action 408 the thermodynamic deviation is determined. Action 408 determines the deviation function by a first deviation, a second deviation, a third deviation, and a fourth deviation.

In action 410 the thermodynamic property is determined. Action 410 determines the thermodynamic property by combining the simple fluid factor, Q factor, and the deviations for the simple fluid, first reference fluid, and second reference fluid. Once the thermodynamic property is determined control passes to action 412.

In action 412 the departure functions are determined. Action 412 determines the enthalpy departure, fugacity departure, and both isobaric and isochoric heat departures for the fluid. Once the departures are determined control passes to action 414 for further processing.

In action 414 the properties are displayed or a control signal is generated. Action 414 takes the output from the different action sequences to generate volumetric, thermodynamic and transport fluid properties. These generated properties could be sent to display device to show the fluid engineer, instrumentations engineer, or operator the properties of the fluid. Further, the same generated signal can be sent to system 100 for further processing. The signal can be processed by a controller 108 (see FIG. 1) to make a determination as to the state of the process. For example, the properties (Volumetric, Thermodynamic, or Transport) can be compared with expected values to ascertain a safe harbor of operation for a given process or machinery. This comparison can be done by defining criteria that can be automatically determined by the controller. This criteria could be based on statistics, averages of outputs, ratios of parameters, or a set of critical parameters like temperature that indicate a process within a tolerable range or safe harbor. The criteria can be easily be implemented as basis for controlling a machine or process through a PID algorithm.

Figure 5:
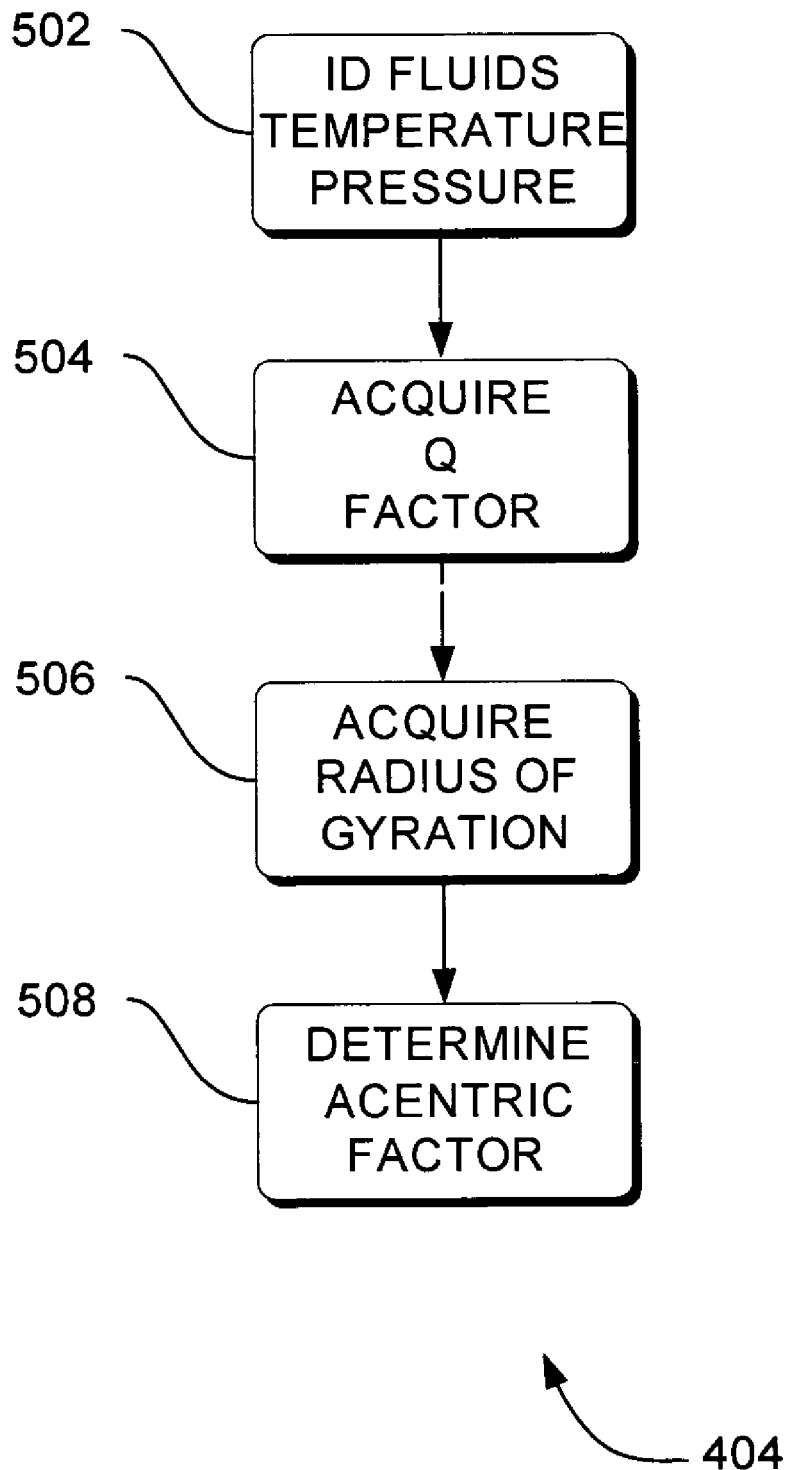
FIG. 5 is a flowchart of a component of the equation of state for determining properties of a fluid.

FIG. 5 is a detailed view of action 404 that acquires operating factors for fluid analysis. Action 404 can be part of a large program, a module, a subroutine, subprogram, procedure, or a library function that can be called by other modules or programs. Method 404 begins with action 502 that identifies the simple fluid, first reference fluid, second reference fluid, temperature, and pressure. After the data is acquired, control passes to action 504 for further processing.

In action 504, the "Q" factor is acquired. The "Q" factor can be acquire from the Yaws database for some selected simple, first reference, and second reference fluid. The value of the "Q" factor has a range from 0.3 to 1.9. If the "Q" factor is not provided by the Yaws database and a value is not provided from prior fluid analyses then a value of 1 is used as a "Q" factor. The reference Q factor ($\Theta^{(o)}$) value of 1.16395 is based on a regression analysis that equates the modified Taylor series compressibility relation to the individual compressibility's of argon, octane and water. The reduced temperature range is from 0.3 to 4, and the reduced pressure range is from 0.01 to 10. The reference Q factor ($\Theta^{(o)}$) for the Transport Properties is of the same magnitude as given for the Volumetric and Thermodynamic Properties estimation. Once the "Q" factor is determined control passes to action 506 for further processing.

In action 506 a radius of gyration is acquired. The radius of gyration ($\sigma$) is acquired from Yaws database. Once the radius of gyration is acquired control passes to action 508 for further processing.

In action 508, the acentric factor is determined. Action 508 determines the acentric factor by first ascertaining the critical and normal boiling point properties for the simple, first reference, and second reference fluids from the Yaws database. The values from Yaws database are then used in the acentric factor formula to determine a value for each of the simple fluid, first reference fluid, and second reference fluid.

Figure 6:
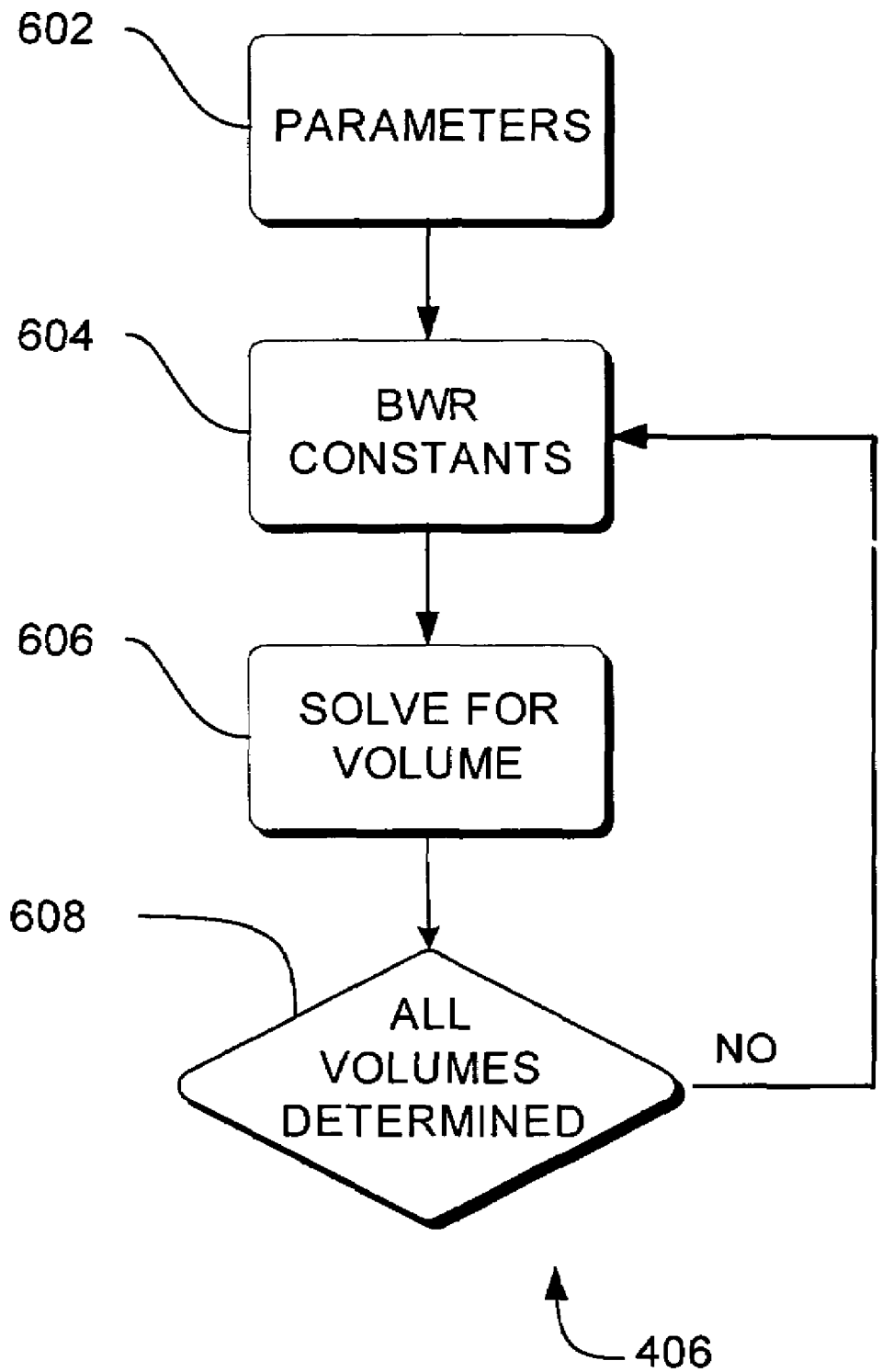
FIG. 6 is a flowchart of molar volume acquisition for the equation of state for determining properties of a fluid.

FIG. 6 is a detailed view of action 406 that determines the molar volume for fluid analysis. Action 406 can be part of a large program, a module, a subroutine, subprogram, procedure, or a library function that can be call by other modules or programs. Method 406 begins with action 602 where the operating parameters of reduced temperature $T_r(T/T_c)$, reduced pressure $P_r(P/P_c)$ are ascertained. Once the operating parameters are determined control passes to action 604 for further processing.

In action 604 the constants for molar volume are acquired. The constants $B_1$ through $B_4$, $C_1$ through $C_4$, $D_1$ through $D_2$, $\beta$, and $\gamma$ are acquired for the simple, first reference and second reference fluids. If the compressibility is known, then action 604 returns a value for the compressibility factor (Z) for each of the fluids and values for the rest of the constants. After the constants are determined control passes to action 606 for further processing.

In action 606 the molar volume is determined. A calculation for the molar volume is done based on the constants acquired in action 604 and the parameters (Tr, Pr) from action 602. If the compressibility factor (Z) is stated then molar volume ($V_r$) is proportional to a ratio of reduced pressure, reduced temperature, and the compressibility factor. In the alternative, the molar volume can be determined by using the constants and either the compressibility factor and ratio of reduced temperature and pressure by substituting possible solutions of molar volume to the modified BWR compressibility equation. Tools such as GOALSEEK and SOLVER for Microsoft Excel® can be used to iteratively determine a value for the molar volume. Once the molar volume is determined in action 606 control passes to action 608 for further processing.

In action 608, all volumes are determined. In action 608, actions 604 through 606 are repeated until the molar volume for the simple fluid, the first reference fluid, and the second reference fluid are determined. Action 608 could be a Boolean expression ("IF", "WHILE", "UNTIL") that is satisfied only when the molar volume for each fluid has been determined. In the alternative, the molar volume could be determined simultaneous by acquiring the constants for the simple, first reference, and second reference fluid at the same time. Once the molar volumes have been determined method 406 is completed.

Figure 7:
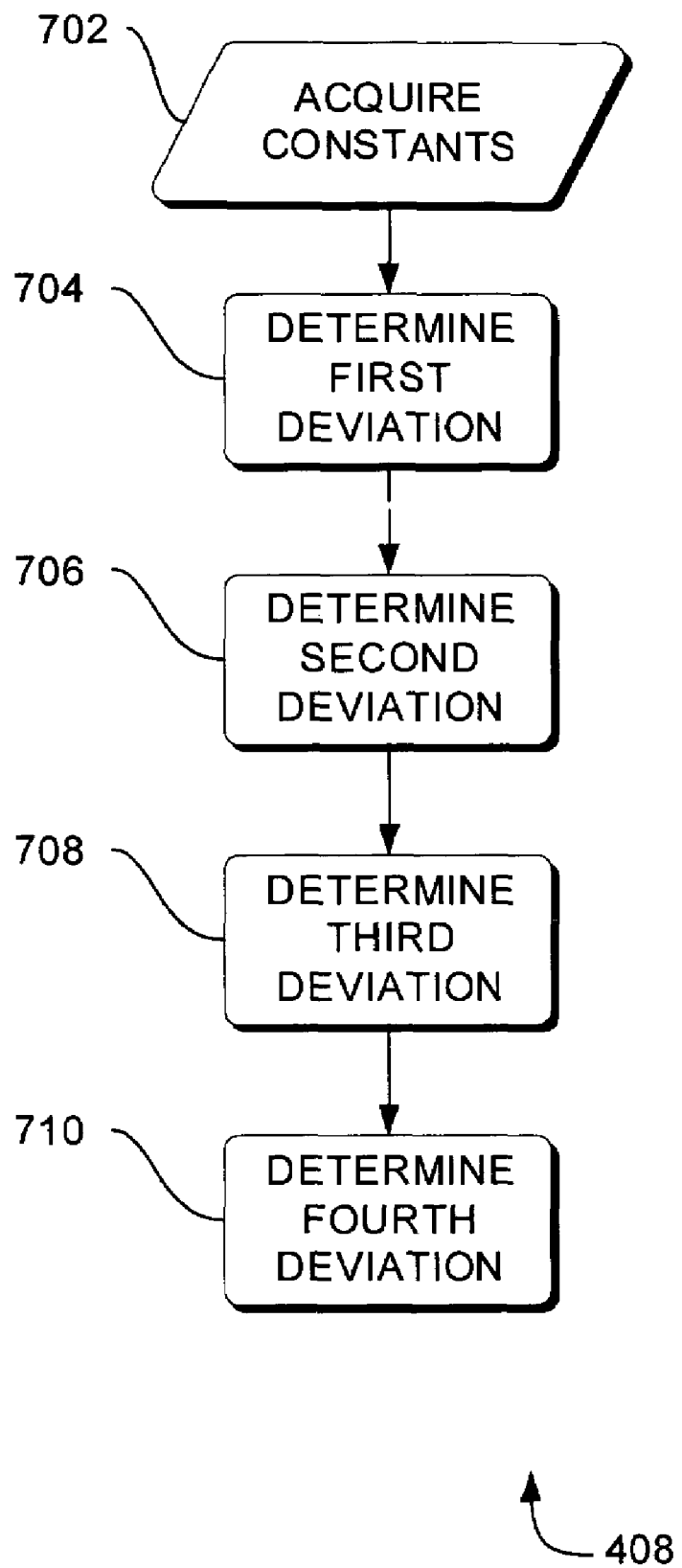
FIG. 7 is a flowchart of thermodynamic deviation for the equation of state for determining properties of a fluid.

FIG. 7 is a detailed view of action 408 that determines the thermodynamic deviation for fluid analysis. Action 408 can be part of a large program, a module, a subroutine, subprogram, procedure, or a library function that can be call by other modules or programs. Method 408 begins with action 702 which acquires constants for performing the calculation.

In action 702 constants are acquired. Action 702 acquires such constants as acentric factor, compressibility, and radius of gyration for the simple, first reference, and second reference fluid at the given molar volume, temperature, and pressure. Once the constants have been determined control passes to action 704 for further processing.

In action 704 a first deviation is determined. Action 704 determines the first deviation by combining the acentric factor and compressibility of the simple fluid and the first reference fluid in accordance to the mathematical relationship described above for the thermodynamic deviation. Once the deviation is determined control passes to action 706 for further processing.

In action 706 a second deviation is determined. Action 706 determines the second deviation by combining the radius of gyration and compressibility of the simple fluid and the first reference fluid in accordance to the mathematical relationship described above for the thermodynamic deviation. Once the second deviation is determined control passes to action 708 for further processing.

In action 708 a third deviation is determined. Action 708 determines the third deviation by combining the acentric factor and compressibility of the simple fluid and the second reference fluid in accordance to the mathematical relationship described above for the thermodynamic deviation. Once the deviation is determined control passes to action 710 for further processing.

In action 710 a fourth deviation is determined. Action 710 determines the fourth deviation by combining the radius of gyration and compressibility of the simple fluid and the second reference fluid in accordance to the mathematical relationship described above for the thermodynamic deviation.

Figure 8:
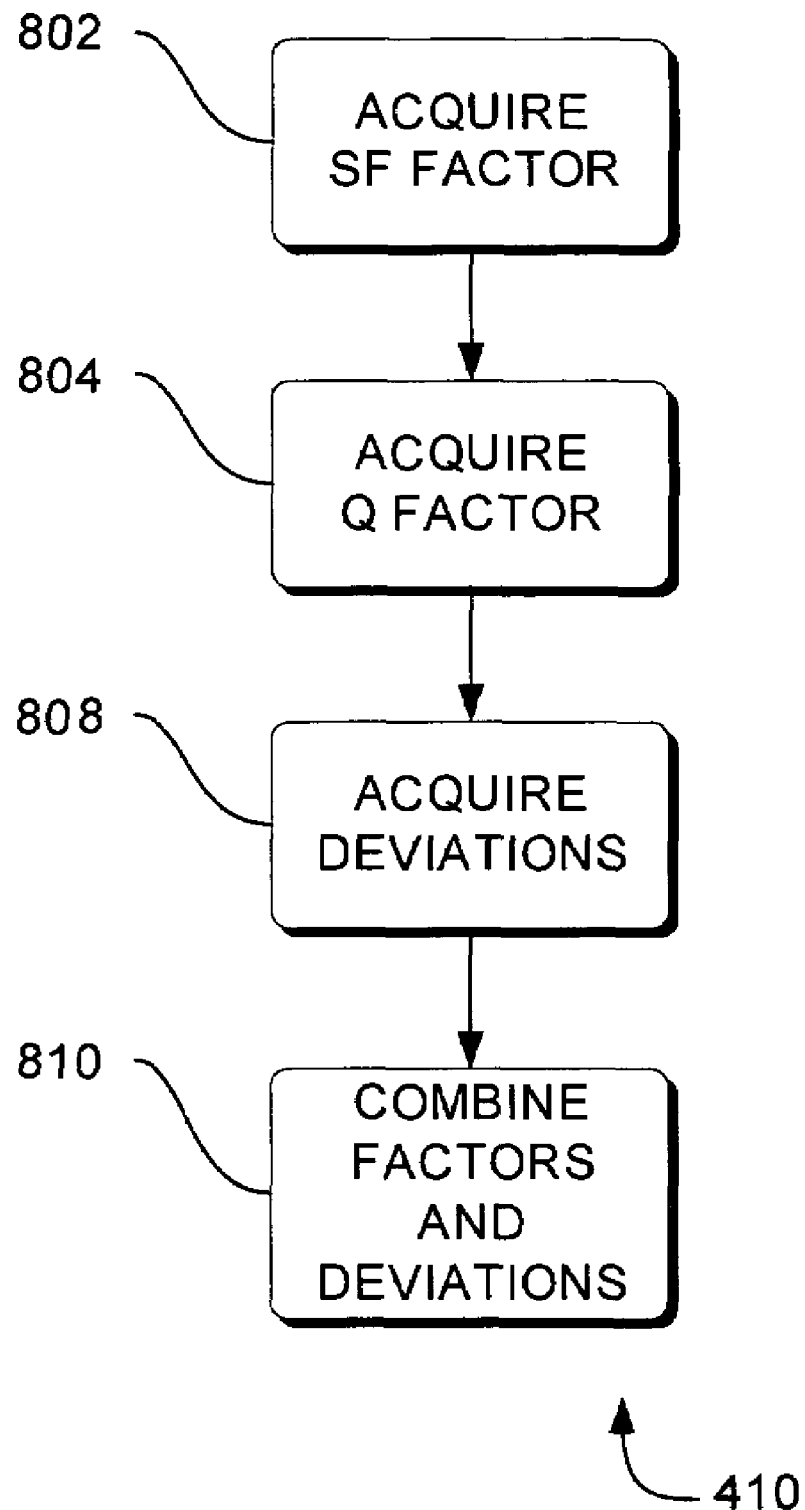
FIG. 8 is a flowchart of thermodynamic property for the equation of state for determining properties of a fluid.

FIG. 8 is a detailed view of action 410 that determines the thermodynamic property for fluid analysis. Action 410 can be part of a large program, a module, a subroutine, subprogram, procedure, or a library function that can be call by other modules or programs. Method 410 begins with action 802 which acquires the compressibility factor for the simple fluid. Once the compressibility factor is determined control passes to action 804 for further processing.

In action 804 a "Q" factor is acquired. Action 804 acquires the "Q" factor from the Yaws database for some selected simple, first reference, and second reference fluid. The value of the "Q" factor is within the range of 0.3 to 1.9. If the "Q" factor is not provided by the Yaws database and a value is not provided from prior fluid analyses then a value of 1 is used as a "Q" factor. The reference Q factor ($\Theta^{(O)}$) value of 1.16395 is used for argon, octane and water and is based on a regression analysis that equates the modified Taylor series compressibility relation to the individual compressibility's of argon, octane and water. The reduced temperature range is from 0.3 to 4, and the reduced pressure range is from 0.01 to 10. The reference Q factor ($\Theta^{(O)}$) for the Transport Properties is of the same magnitude as given for the Volumetric and Thermodynamic Properties estimation. Once the "Q" factor is determined control passes to action 808 for further processing.

In action 808 the deviations are acquired. Action 808 acquires the deviation determined in method 408 in FIG. 7. Once the deviations are acquired control passes to action 810 for further processing.

In action 810 the factors and deviations are combined. Action 810 combines the factors and deviations in the proportion shown above for determining thermodynamic property.

Figure 9:
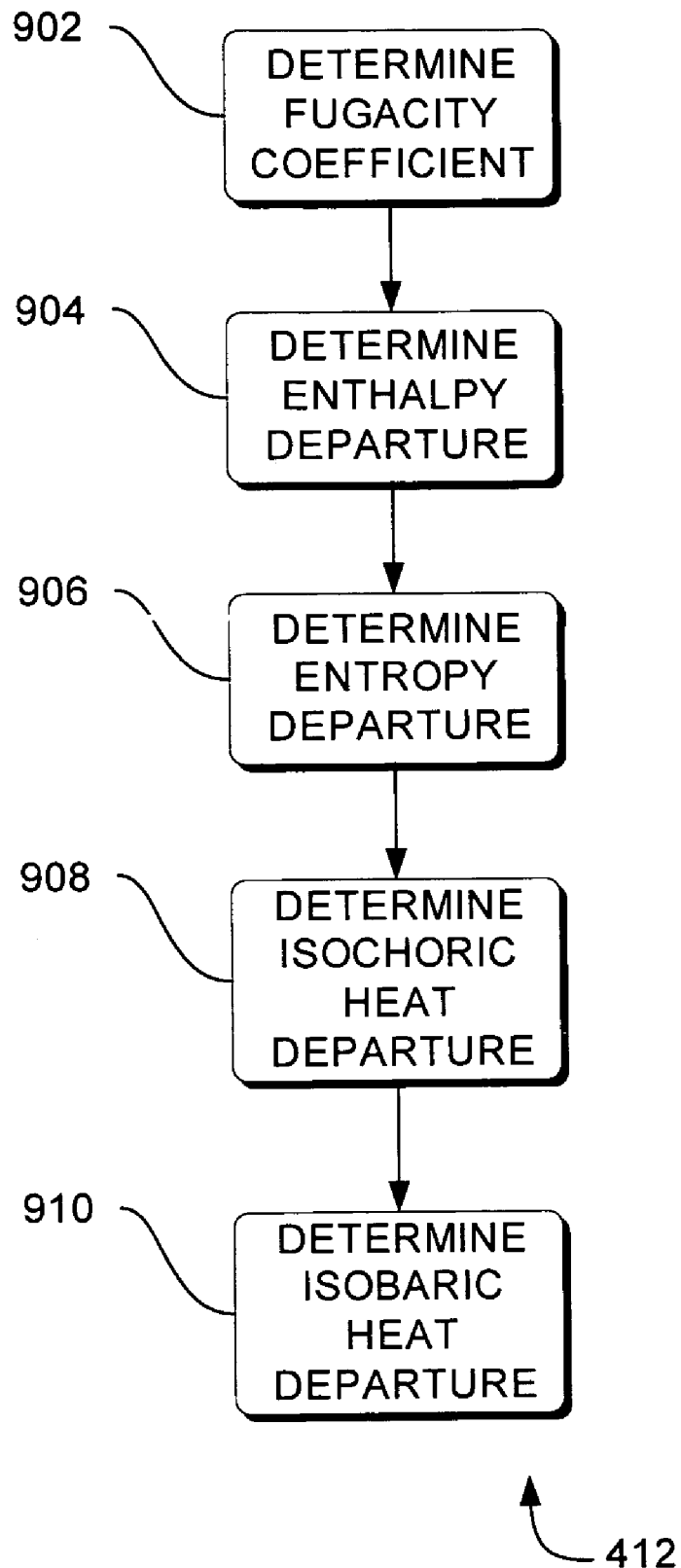
FIG. 9 is a flowchart of departure function determination for the equation of state for determining properties of a fluid.

FIG. 9 is a detailed view of action 412 that determines the departure functions for fluid analysis. The departure functions for the thermodynamic property, simple fluid, first reference fluid, and second reference fluid are individually determined. One first applies the departure-function formalism to each of the simple fluid, first reference fluid, and second reference fluid of a mixture; then reuses the departure function for the mixture as a whole. In the application to components, one expresses the reference-state enthalpy and entropy as finite series of temperature- and pressure-dependent terms, the coefficients of which are established by least squares fits to the best available empirical data on enthalpy and entropy. Action 412 can be part of a large program, a module, a subroutine, subprogram, procedure, or a library function that can be call by other modules or programs. Method 412 begins with action 902 and passes control to action 904 upon completion.

In action 902, the fugacity coefficient is determined. The fugacity coefficient gives the deviation of the pressure of a real fluid from the pressure of an ideal fluid at given volume and temperature. The fugacity coefficient is thus a measure of non-ideality. The fugacity coefficient is determined by use of the molar volume ($V_r$), constants acquired in action 604, a constant E, and the operating parameters such as temperature and pressure. Once the fugacity coefficient is determined control passes to action 904 for further processing.

In action 904, the enthalpy departure is determined. The enthalpy departure (H–H°) expresses the difference between an ideal fluid and a selected fluid and is mathematical expressed by the above relationship. Action 904 determines departure form the temperature, pressure, compressibility, and the determined molar volume. Once the enthalpy departure has been calculated control passes to action 906 for further processing.

In action 906 the entropy departure is determined. Action 906 determines the entropy departure by solving the mathematical relationship above for entropy departure. Once the entropy departure is determined control passes to action 908 for further processing.

In action 908 isochoric heat departure is determined. Action 908 determines the isochoric heat departure by solving the mathematical relationship above for isochoric heat departure. Once the entropy departure is determined control passes to action 910 for further processing.

In action 910 isobaric heat departure is determined. Action 910 determines the isobaric heat departure by solving the mathematical relationship above for isobaric heat departure.

Figure 10:
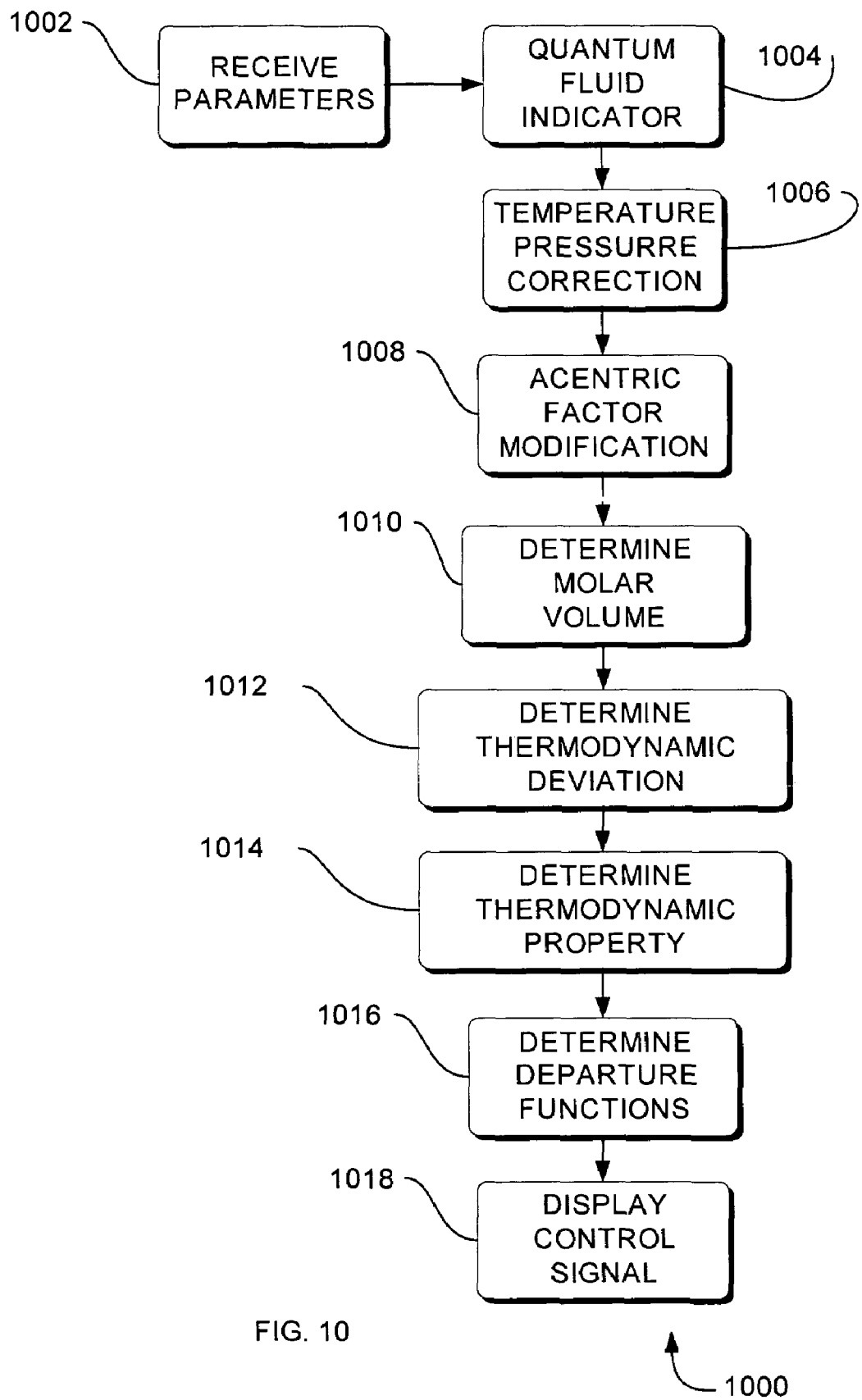
FIG. 10 is a flowchart for determining the equation of state for determining properties of a quantum fluid.

FIG. 10 is a flowchart of a method performed by a client according to an embodiment. Method 1000 satisfies the need in the art for performing fluid analyses in real-time with minimal interference to the operating environment. Method 1000 can be used to control, in conjunction with controllers, actuators, valves, and other devices chemical process control system 100. Method 1000 begins with action 1002 by receiving parameters to start the fluid analysis.

In action 1002 parameters are received. The received parameters can be one or a combination of temperature, pressure, simple fluid, first reference fluid, second reference fluid, an indication that the fluid is a quantum fluid, Q factor, fluid flow, volume flow, operating environment of the fluid. The received parameters can be inputted through a keyboard 318, pointing device 320, portable digital assistance (PDA), and remote terminal, directly measured from a process or machine, derived from any of the above parameters. Once the parameters have been received control passes to action 1004 for further processing.

In action 1004 a quantum fluid indication is made. Action 1004 acquires a "yes" or "no" indication that the fluid is a quantum fluid. The indication can be the form of a "1" or "0", selected indicia, the albescence or presence of a value, or inferential based on the value of the acentric factor. Once action 1004 acquires quantum fluid indication control passes to action 1006 for further processing.

In action 1006, the reduced temperature and pressure are corrected for quantum fluid. Action 1006 corrects the acquired reduced temperature and pressure for quantum fluid analyses using Gunn's relation. In Gunn's relation, the corrected reduced temperature is function of the reduced temperature and molecular weight; the corrected reduced pressure is a function of the reduced temperature, the reduced pressure, and molecular weight. Once these reduced temperature and pressure are corrected, control passes to action 1008 for further process.

In action 1008 acentric factor is modified. Action 1008 modifies the acentric factor by setting it to zero or substantially zero. If the parameters are initially set by the operator or user of the fluid analysis system, acentric factor would most likely be set to zero. However, in instances were the acentric factor is determined by the mathematical relationship above then the value returned by that module will be set to zero for quantum fluid analysis. Once the acentric factor is modified control passes 1010 for further processing. In action 1010 the molar volume is determined. Action 1010 the parameters and operating condition are used to determine the molar volume for the simple fluid, the first reference fluid, and the second reference fluid. After the volumes are determined control passes to action 1012 for further processing.

In action 1012 the thermodynamic deviation is determined. Action 1012 determines the deviation function by a first deviation, a second deviation, a third deviation, and a fourth deviation. Control then passes to action 1014 for further processing.

In action 1014 the thermodynamic property is determined. Action 1014 determines the thermodynamic property by combining the simple fluid factor, Q factor, and the deviations for the simple fluid, first reference fluid, and second reference fluid. Once the thermodynamic property is determined control passes to action 1016.

In action 1016 the departure functions are determined. Action 1016 determines the enthalpy departure, fugacity departure, and both isobaric and isochoric heat departures for the fluid. Once the departures are determined control passes to action 1018 for further processing.

In action 1018 the properties are displayed or a control signal is generated. Action 1018 takes the output from the different action sequences to generate volumetric, thermodynamic and transport fluid properties. These generated properties could be sent to display device to show the fluid engineer, instrumentations engineer, or operator the properties of the fluid. Further, the same generated signal can be sent to system 100 for further processing. The signal can be processed by a controller 108 (see FIG. 1) to make a determination as to the state of the process. For example, the properties (volumetric, thermodynamic, or transport) can be compared with expected values to ascertain a safe harbor of operation for a given process or machinery. This comparison can be done by defining criteria that can be automatically determined by the controller. This criteria could be based on statistics, averages of outputs, ratios of parameters, or a set of critical parameters like temperature that indicate a process within a tolerable range or safe harbor. The criteria can be easily be implemented as basis for controlling a machine or process through a PID algorithm.

Method 1000 has been described with reference to actions 1002 through 1018. The difference between these actions and those of method 400 are in the arguments, parameters that are used in calling the individual functions. For example, the determination of molar volume in action 1010 and molar volume in action 406 differs in the parameters passed as arguments to the module, function, or subroutine.

Figure 11:
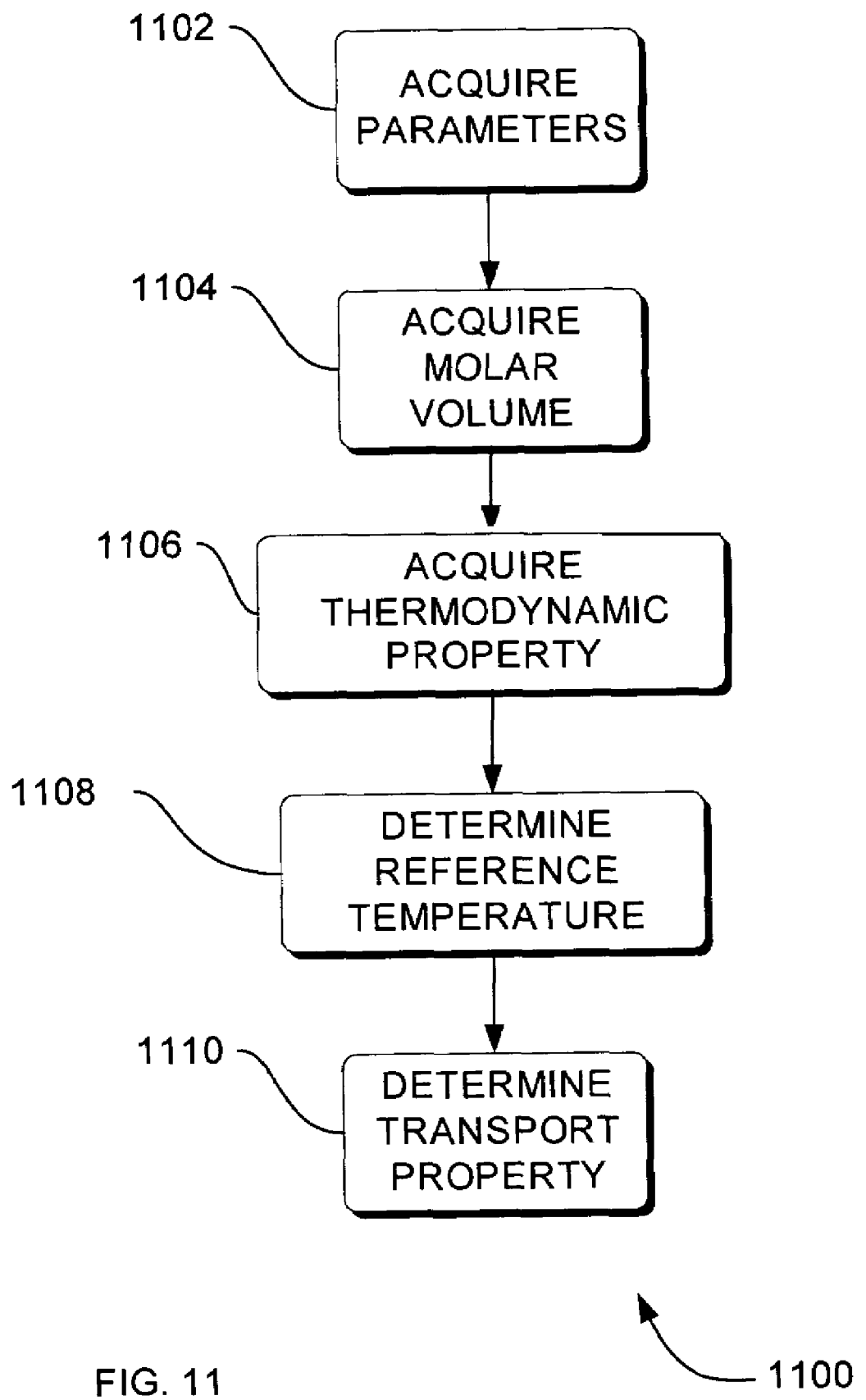
FIG. 11 is a flowchart for determining parameters such as volumetric flow for the equation of state.

FIG. 11 is a flowchart of a method performed by a client according to an embodiment. In particular, method 1100 determines transport property analysis in order to ascertain viscosity, thermal conductivity and surface tension parameters. Method 1100 satisfies the need in the art for performing fluid analyses in real-time with minimal interference to the operating environment. Method 1100 can be used to control, in conjunction with controllers, actuators, valves, and other devices chemical process control system 100. Method 1100 begins with action 1102 by receiving parameters to start the fluid analysis.

In action 1102 parameters are acquired: The acquired parameters can be a one or combination of temperature, pressure, simple fluid, first reference fluid, second reference fluid, an indication that the fluid is a quantum fluid, Q factor, fluid flow, volume flow, operating environment of the fluid. The received parameters can be inputted through a keyboard 318, pointing device 320, portable digital assistance (PDA), and remote terminal, directly measured from a process or machine, derived from any of the above parameters. Once the parameters have been received control passes to action 1104 for further processing.

In action 1104, the molar volume is acquired. Action 1104 the parameters and operating condition are used to determine the molar volume for the simple fluid, the first reference fluid, and the second reference fluid. After the volumes are determined control passes to action 1106 for further processing.

In action 1106, thermodynamic property is acquired. Action 1106 either uses the determination of thermodynamic property from method 400 or method 1000 for a quantum fluid, or calls upon these methods with the acquired parameters as argument to determine the thermodynamic property for the desired parameters. In the alternative, it is envisioned that the thermodynamic property could be acquired from an external source like a database or calculated by other equations of state. After thermodynamic property is determined control passes to action 1108 for further processing.

In action 1108, reference temperature is determined. Action 1108 corrects the acquired temperature in action 1102 so as to reflect a ratio to the critical temperature of the components of the simple fluid, first reference fluid, and second reference fluid. Once the reference temperature is determined control passes to action 1110 for further processing.

In action 1110, transport property is determined. Action 1110 determines the viscosity, thermal conductivity, and surface tension for each of the components of the fluid in accordance with the log reduced transport property enumerated above.

In some embodiments, methods 400–1100 are implemented as a computer data signal embodied in a carrier wave, that represents a sequence of instructions which, when executed by a processor, such as processor 304 in FIG. 3, cause the processor to perform the respective method. In other embodiments, methods 400–1100 are implemented as a computer-accessible medium having executable instructions capable of directing a processor, such as processor 304 in FIG. 3, to perform the respective method. In varying embodiments, the medium is a magnetic medium, an electronic medium, or an optical medium.

Implementation

Figure 12:
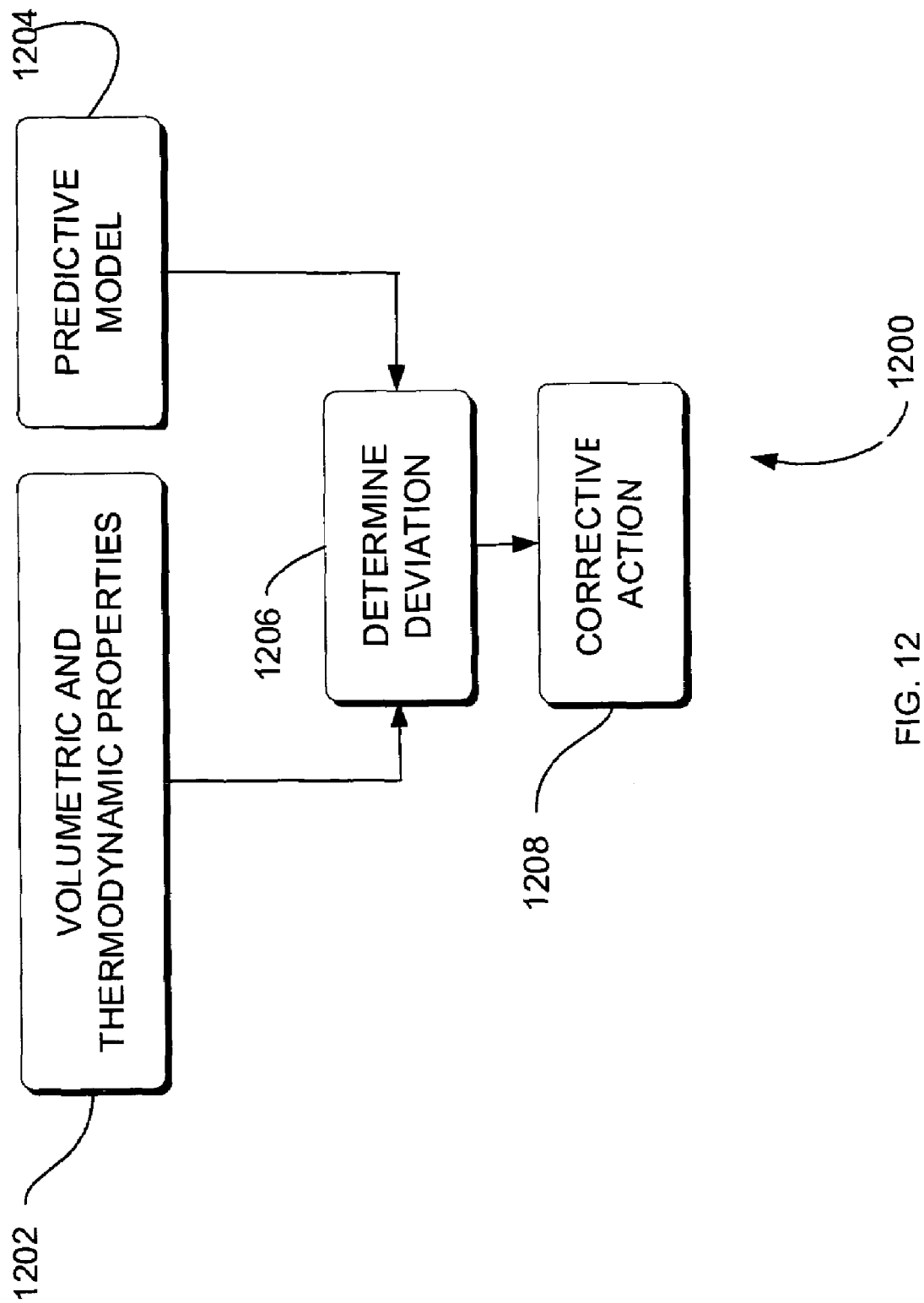
FIG. 12 is a flowchart of a method for determining deviation of a process and suggesting corrective action for the process based on the equation of state.

Referring to FIG. 12, a particular implementation 1200 is described in conjunction with the system overview in FIG. 1 and the methods described in conjunction with FIGS. 4, 10 and 11 that are methods 400, 1000 and 1100.

FIG. 12 is a block diagram that provides a system level overview for a system to determine if a machine or chemical process is performing within acceptable levels. Block 1202 represents parameters of the machine or chemical process such as volumetric, thermodynamic or transport properties that are physically determined or derived through the equation of state following methods 400, 1000, 1100 as outline above. For example the temperature, pressure can be measured directly and the other properties could be derived from the equation of state. Block 1204 represents the predictive model for the fluid assuming no degradation or additive for the chosen fluid. For example in the analysis of lubricant of an engine, the oil changes during machine use due to contamination and, frequently, due to temperature spikes.

Block 1206 receives at least one of the volumetric, thermodynamic, or transport properties from the machine or process as it operates and from the predictive model so as to determine a deviation. The deviation could be statistical, a percentage, an amount, or a ratio of a parameter. This deviation could be determined by a properly programmed general purpose computer. In the alternative, the deviation could be a dedicated circuit such as a comparator with plural inputs that would compare the predictive value with the in situ values from a machine or process.

Block 1208 receives the deviation from block 1206 and takes corrective action to bring the machine or process to an acceptable point of operation. The deviation could be a series of values that is sent to a controller or computer that can based on preset values determine if action needs to be initiated. In the case of an engine it can be to add more lubricant, cease operation, schedule a maintenance stop, and generate an alarm signal so an operator can take corrective action. In the case of a process it can be a signal sent to a PID controller that can interpret to activate actuators or valves.

The system 1200 components of the 1202, 1204, 1206 and the corrective 1208 can be embodied as computer hardware circuitry or as a computer-readable program, or a combination of both. In another embodiment, system 1200 is implemented in an application service provider (ASP) system.

More specifically, in the computer-readable program embodiment, the programs can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (API) or interprocess communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in computer 208 in FIG. 3, or on at least as many computers as there are components.

CONCLUSION

A fluid analysis system and method has been described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, although described in object-oriented terms, one of ordinary skill in the art will appreciate that implementations can be made in a procedural design environment or any other design environment that provides the required relationships.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types.

The terminology used in this application with respect to module, functions, procedures, and subroutine is meant to include all object-oriented, database and communication environments and alternate technologies which provide the same functionality as described herein.

We claim:

1. A computerized method for determining one or more properties of a multi-component fluid comprising:
    receiving information indicative of the physical properties of a simple fluid, a first reference fluid, and a second reference fluid;
    collecting based on the received information indicative of the physical properties of a simple fluid, first reference fluid, and second reference fluid operating parameters;
    determining the molar volume of the simple fluid, first reference fluid, and second reference fluid from the received information and acquired operating parameters;
    determining a departure function from the received information and operating parameters for the simple fluid, first reference fluid, and second reference fluid;
    determining thermodynamic deviation from a combination of the departure function and acquired operating parameters;
    determining one or more properties of a multicomponent fluid from the departure function, the thermodynamic deviation, and the determined molar volume; and
    displaying the determined one or more properties of a multicomponent fluid.

2. The computerized method of claim 1, wherein collecting fluid operating parameters is at least one of temperature and pressure, a Q factor, radius of gyration, acentric factor.

3. The computerized method of claim 2, wherein the Q factor has a numerical value of up to two.

4. The computerized method of claim 2, wherein the radius of gyration is collected from the Yaws database.

5. The computerized method of claim 2, wherein the acentric factor is calculated from Yaws database properties of the simple fluid, first reference fluid, and second reference fluid.

6. The computerized method of claim 2, wherein determining the molar volume is based on collected constants from the Benedict-Webb-Rubin database of values for the simple fluid, first reference fluid, and second reference fluid.

7. The computerized method of claim 2, wherein determining the departure function is at least one of fugacity coefficient, enthalpy departure, entropy departure, isochoric heat capacity departure, isobaric heat capacity departure.

8. The computerized method of claim 7, wherein determining the thermodynamic deviation consist of a first deviation, a second deviation, a third deviation, a fourth deviation.

9. The computerized method of claim 8, wherein the first deviation is a function of the acentric factor of the simple fluid and the first reference fluid, and the thermodynamic deviation of the simple fluid and the first reference fluid.

10. The computerized method of claim 8, wherein the second deviation is a function of the radius of gyration of the simple fluid and the first reference fluid, and the thermodynamic deviation of the simple fluid and the first reference fluid.

11. The computerized method of claim 8, wherein the third deviation is a function of the acentric factor of the simple fluid and the second reference fluid, and the thermodynamic deviation of the simple fluid and the second reference fluid.

12. The computerized method of claim 8, wherein the fourth deviation is a function of the radius of gyration of the simple fluid and the second reference fluid, and the thermodynamic deviation of the simple fluid and the second reference fluid.

13. The computerized method of claim 8, wherein the determining of the property is a combination of a simple fluid factor, the Q factor, and the determined thermodynamic deviation.

14. The computerized method of claim 13, wherein the determining of the property is the transport properties of the multi-component fluid.

15. A computerized method for determining one or more properties of a multi-component fluid comprising:
  selecting an indicator that characterizes the fluid as one of polar fluid, non-polar fluid;
  receiving information indicative of the physical properties of a simple fluid, a first reference fluid, and a second reference fluid;
  collecting based on the selected indicator and the received information indicative of the physical properties of a simple fluid, a first reference fluid, and a second reference fluid operating parameter;
  determining the molar volume of the simple fluid, first reference fluid, and second reference fluid from the received information and acquired operating parameters;
  determining a departure function from the received information and operating parameters for the simple fluid, first reference fluid, and second reference fluid;
  determining thermodynamic deviation from a combination of the departure function and acquired operating parameters;
  determining one or more properties of a multicomponent fluid from the departure function, the thermodynamic deviation, and the determined molar volume; and
  displaying the determined one or more properties of a multicomponent fluid.

16. The computerized method of claim 15, wherein the fluid operating parameters further comprise at least one of temperature and pressure, a Q factor, radius of gyration, acentric factor; and
  when a characterization of non-polar fluid is selected assigning a substantially value of zero to the acentric factor and correcting the temperature and pressure by a reduction factor.

17. The computerized method of claim 16, wherein the Q factor has a numerical value of up to two.

18. The computerized method of claim 16, wherein the radius of gyration is collected from the Yaws database.

19. The computerized method of claim 16, wherein the acentric factor is calculated from Yaws database properties of the simple fluid, first reference fluid, and second reference fluid.

20. The computerized method of claim 16, wherein determining the molar volume is based on collected constants from the Benedict-Webb-Rubin database of values for the simple fluid, first reference fluid, and second reference fluid.

21. The computerized method of claim 16, wherein determining the departure function is at least one of fugacity coefficient, enthalpy departure, entropy departure, isochoric heat capacity departure, isobaric heat capacity departure.

22. The computerized method of claim 21, wherein determining the thermodynamic deviation consist of a first deviation, a second deviation, a third deviation, a fourth deviation.

23. The computerized method of claim 22, wherein the first deviation is a function of the acentric factor of the simple fluid and the first reference fluid, and the thermodynamic deviation of the simple fluid and the first reference fluid.

24. The computerized method of claim 22, wherein the second deviation is a function of the radius of gyration of the simple fluid and the first reference fluid, and the thermodynamic deviation of the simple fluid and the first reference fluid.

25. The computerized method of claim 22, wherein the third deviation is a function of the acentric factor of the simple fluid and the second reference fluid, and the thermodynamic deviation of the simple fluid and the second reference fluid.

26. The computerized method of claim 22, wherein the fourth deviation is a function of the radius of gyration of the simple fluid and the second reference fluid, and the thermodynamic deviation of the simple fluid and the second reference fluid.

27. The computerized method of claim 22, wherein the determining of the property is a combination of a simple fluid factor, the Q factor, and the determined thermodynamic deviation.

28. The computerized method of claim 27, wherein the determining of the property is the transport properties of the multi-component fluid.

29. A computer-accessible medium having executable instructions to determine one or more properties of a multi-component fluid, the executable instructions capable of directing a processor to perform:

selecting an indicator that characterizes the fluid as one of polar fluid, non-polar fluid;

receiving information indicative of the physical properties of a simple fluid, a first reference fluid, and a second reference fluid;

collecting based on the selected indicator and the received information indicative of the physical properties of a simple fluid, first reference fluid, and second reference fluid operating parameters;

determining the molar volume of the simple fluid, first reference fluid, and second reference fluid from the received information and acquired operating parameters;

determining a departure function from the received information and operating parameters for the simple fluid, first reference fluid, and second reference fluid;

determining thermodynamic deviation from a combination of the departure function and acquired operating parameters;

determining one or more properties of a multicomponent fluid from the departure function, the thermodynamic deviation, and the determined molar volume; and displaying the determined one or more properties of a multicomponent fluid.

30. The computer accessible medium of claim 29, wherein the determining of the property is a combination of a simple fluid factor, a Q factor, and a determined thermodynamic deviation function consisting of two or more components.

31. An article of manufacture comprising:

a computer useable medium having a computer readable code means embodied in said medium for determining one or more properties of a multi-component fluid, the computer readable program code in said article of manufacture comprising:

computer readable program code means for causing a computer to perform the function of:

selecting an indicator that characterizes the fluid as one of polar fluid, non-polar fluid;

receiving information indicative of the physical properties of a simple fluid, a first reference fluid, and a second reference fluid;

collecting based on the selected indicator and the received information indicative of the physical properties of a simple fluid, first reference fluid, and second reference fluid operating parameters;

determining the molar volume of the simple fluid, first reference fluid, and second reference fluid from the received information and acquired operating parameters;

determining a departure function from the received information and operating parameters for the simple fluid, first reference fluid, and second reference fluid;

determining thermodynamic deviation from a combination of the departure function and acquired operating parameters;

determining one or more properties of a multicomponent fluid from the departure function, the thermodynamic deviation, and the determined molar volume; and displaying the determined one or more properties of a multicomponent fluid.

32. The article of manufacture of claim 31, wherein the determining of the property is a combination of a simple fluid factor, a Q factor, and a determined thermodynamic deviation function consisting of two or more components.

33. A method of executing real-time control of a process through analyses of one or more properties of a fluid, comprising the actions of:

providing an interactive modeler that models the equation of state for the fluid in the process based on measured signals and for selectively enabling the modeling of control changes to the process;

receiving input signals which represent measured parameter values for a fluid from a plurality of sensors;

periodically transmitting said measured parameter values to an interactive modeler having a process model that models the equation of state for the fluid in the process;

estimating one or more properties for the fluid from at least one unmeasured process parameter in said interactive modeler from said process model;

disturbance error model for predicting the difference between the estimated one or more properties of the fluid and the expected one or more properties of the fluid;

determining a set of current and future manipulated parameter values which will minimize the predicted difference between the estimated one or more properties and the expected one or more properties of the fluid;

displaying the estimated one or more properties of the fluid; and causing a process control device electrically coupled to said process to control the process based on said manipulated parameter values.

34. The method of claim 33, wherein interactive modeler that models the equation of state for the fluid consists of a combination of a simple fluid factor, a Q factor, and a determined thermodynamic deviation function consisting of two or more components.

35. The method of claim 34, wherein the property of the fluid is one of transport properties, thermodynamic property.

36. A system to perform fluid analysis comprising:

a processor;

a storage device coupled to the processor; and software means embedded in the storage device and operative on the processor operable to:

receive information indicative of the physical properties of a simple fluid, a first reference fluid, and a second reference fluid;

collect based on the received information indicative of the physical properties of a simple fluid, first reference fluid, and second reference fluid operating parameters;

determine the molar volume of the simple fluid, first reference fluid, and second reference fluid from the received information and acquired operating parameters;

determine a departure function from the received information and operating parameters for the simple fluid, first reference fluid, and second reference fluid;

determine thermodynamic deviation from a combination of the departure function and acquired operating parameters; and determine one or more properties of a multicomponent fluid from the departure function, the thermodynamic deviation, and the determined molar volume;

display the determined one or more properties of a multicomponent fluid.

37. The system of claim 36, wherein collecting fluid operating parameters is at least one of temperature and pressure, a Q factor, radius of gyration, acentric factor.

38. The system of claim 37, wherein the Q factor has a numerical value of up to two.

39. The system of claim 37, wherein the radius of gyration is collected from the Yaws database.

40. The system of claim 37, wherein the acentric factor is calculated from Yaws database properties of the simple fluid, first reference fluid, and second reference fluid.

41. The system of claim 37, wherein determining the molar volume is based on collected constants from the Benedict-Webb-Rubin database of values for the simple fluid, first reference fluid, and second reference fluid.

42. The system of claim 37, wherein determining the departure function is at least one of fugacity coefficient, enthalpy departure, entropy departure, isochoric heat capacity departure, isobaric heat capacity departure.

43. The system of claim 42, wherein determining the thermodynamic deviation consist of a first deviation, a second deviation, a third deviation, a fourth deviation.

44. The system of claim 43, wherein the first deviation is a function of the acentric factor of the simple fluid and the first reference fluid, and the thermodynamic deviation of the simple fluid and the first reference fluid.

45. The system of claim 43, wherein the second deviation is a function of the radius of gyration of the simple fluid and the first reference fluid, and the thermodynamic deviation of the simple fluid and the first reference fluid.

46. The system of claim 43, wherein the third deviation is a function of the acentric factor of the simple fluid and the second reference fluid, and the thermodynamic deviation of the simple fluid and the second reference fluid.

47. The system of claim 43, wherein the fourth deviation is a function of the radius of gyration of the simple fluid and the second reference fluid, and the thermodynamic deviation of the simple fluid and the second reference fluid.

48. The system of claim 43, wherein the determining of the property is a combination of a simple fluid factor, the Q factor, and the determined thermodynamic deviation.

49. The system of claim 48, wherein the determining of the property is the transport properties of the multi-component fluid.

50. A computerized system comprising:
a processor;
a storage device coupled to the processor;
an input/output interface coupled to the processor; and
software means embedded in the storage device and operative on the processor operable to:
select an indicator that characterizes the fluid as one of polar fluid, non-polar fluid;
receive information indicative of the physical properties of a simple fluid, a first reference fluid, and a second reference fluid;
collect based on the selected indicator and the received information indicative of the physical properties of a simple fluid, first reference fluid, and second reference fluid operating parameters;
determine the molar volume of the simple fluid, first reference fluid, and second reference fluid from the received information and acquired operating parameters;
determine a departure function from the received information and operating parameters for the simple fluid, first reference fluid, and second reference fluid;
determine thermodynamic deviation from a combination of the departure function and acquired operating parameters; and
determine one or more properties of a multicomponent fluid from the departure function, the thermodynamic deviation, and determined molar volume;
display the determined one or more properties of a muiticomponent fluid.

51. The computerized system of claim 50, wherein collecting fluid operating parameters is at least one of temperature and pressure, a Q factor, radius of gyration, acentric factor; and
when a characterization of non-polar fluid is selected assigning a substantially value of zero to the acentric factor and correcting the temperature and pressure by a reduction factor.

52. The computerized system of claim 51, wherein the Q factor has a numerical value of up to two.

53. The computerized system of claim 51, wherein the radius of gyration is collected from the Yaws database.

54. The computerized system of claim 51, wherein the acentric factor is calculated from Yaws database properties of the simple fluid, first reference fluid, and second reference fluid.

55. The computerized system of claim 51, wherein determining the molar volume is based on collected constants from the Benedict-Webb-Rubin database of values for the simple fluid, first reference fluid, and second reference fluid.

56. The computerized system of claim 51, wherein determining the departure function is at least one of fugacity coefficient, enthalpy departure, entropy departure, isochoric heat capacity departure, isobaric heat capacity departure.

57. The computerized system of claim 56, wherein determining the thermodynamic deviation consist of a first deviation, a second deviation, a third deviation, a fourth deviation.

58. The computerized system of claim 57, wherein the first deviation is a function of the acentric factor of the simple fluid and the first reference fluid, and the thermodynamic deviation of the simple fluid and the first reference fluid.

59. The computerized system of claim 57, wherein the second deviation is a function of the radius of gyration of the simple fluid and the first reference fluid, and the thermodynamic deviation of the simple fluid and the first reference fluid.

60. The computerized system of claim 57, wherein the third deviation is a function of the acentric factor of the simple fluid and the second reference fluid, and the thermodynamic deviation of the simple fluid and the second reference fluid.

61. The computerized system of claim 57, wherein the fourth deviation is a function of the radius of gyration of the simple fluid and the second reference fluid, and the thermodynamic deviation of the simple fluid and the second reference fluid.

62. The computerized system of claim 57, wherein the determining of the property is a combination of a simple fluid factor, the Q factor, and the determined thermodynamic deviation.

63. The computerized system of claim 62, wherein the determining of the property is the transport properties of the multi-component fluid.

64. An apparatus for monitoring the health of a machine through analyses of one or more properties of a fluid, the apparatus comprises:
a modeler that models the equation of state for the fluid in the machine based on measured signals;
a sequencer having a processor;
a storage device coupled to the processor; and software means embedded in the storage device and operative on the processor operable to:

receive input signals which represent measured parameter values for a fluid from a plurality of sensors;

transmit said measured parameter values to said a modeler having a process model that models the equation of state for the fluid in the machine;

receive one or more properties for the fluid from at least one unmeasured machine parameter in said modeler from said process model;

determine the difference between the received input signals which represent measured parameter values and the received one or more properties for the fluid from at least one unmeasured machine parameter from the modeler;

determine if the difference is beyond a predetermined set point;

generate a machine health signal based on the determined difference, wherein a difference that is less than the predetermined set point is an indication of machine health.

65. The apparatus of claim 64, wherein the modeler that models the equation of state for the fluid consist of a combination of a simple fluid factor, a Q factor, and a determined thermodynamic deviation function consisting of two or more components.

66. The apparatus of claim 65, wherein the property of the fluid is one of transport properties, thermodynamic property.

* * * * *